(12) United States Patent
Stad et al.

(10) Patent No.: US 9,387,017 B2
(45) Date of Patent: Jul. 12, 2016

(54) SYSTEM AND METHOD FOR MANIPULATING A SPINAL CONSTRUCT

(71) Applicant: DePuy Synthes Products, Inc., Raynham, MA (US)

(72) Inventors: Shawn D. Stad, Fall River, MA (US); Garth G. Baker, Somerset, MA (US); Tony Tannoury, Andover, MA (US); Paul G. Beaudoin, Derry, NH (US); Christopher Ramsay, West Wareham, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 535 days.

(21) Appl. No.: 13/869,059

(22) Filed: Apr. 24, 2013

(65) Prior Publication Data

US 2013/0238037 A1    Sep. 12, 2013

Related U.S. Application Data

(62) Division of application No. 12/168,455, filed on Jul. 7, 2008, now Pat. No. 8,444,649.

(51) Int. Cl.
*A61B 17/70*    (2006.01)

(52) U.S. Cl.
CPC ........... *A61B 17/7074* (2013.01); *A61B 17/708* (2013.01); *A61B 17/7032* (2013.01)

(58) Field of Classification Search
CPC .................................. A61B 17/7074–17/7092
USPC ................................................ 606/86 A, 86 R
See application file for complete search history.

(56) References Cited

U.S. PATENT DOCUMENTS

| | | | |
|---|---|---|---|
| 5,531,751 A | 7/1996 | Schultheiss et al. | |
| 6,090,113 A | 7/2000 | Le Couedic et al. | |
| 6,551,316 B1 | 4/2003 | Rinner et al. | |
| 6,589,250 B2 | 7/2003 | Schendel | |
| 6,969,392 B2 | 11/2005 | Gitis et al. | |
| 7,008,432 B2 | 3/2006 | Schlapfer et al. | |
| 2001/0029377 A1 | 10/2001 | Aebi et al. | |
| 2004/0024411 A1 | 2/2004 | Newton et al. | |
| 2004/0210232 A1 | 10/2004 | Patel et al. | |
| 2005/0021040 A1 | 1/2005 | Bertagnoli | |
| 2005/0154389 A1 | 7/2005 | Selover et al. | |
| 2005/0171551 A1* | 8/2005 | Sukovich | A61B 17/0218 606/86 R |
| 2005/0273167 A1 | 12/2005 | Triplett et al. | |
| 2006/0004380 A1 | 1/2006 | DiDomenico et al. | |

(Continued)

FOREIGN PATENT DOCUMENTS

EP        1767161 A1    3/2007

*Primary Examiner* — Nicholas Plionis
(74) *Attorney, Agent, or Firm* — Nutter McClennen & Fish LLP

(57) ABSTRACT

A system and device for manipulating a spinal construct is provided. For example, the manipulation device can include a drive member to be disposed within a first surgical sleeve extending from a first vertebra, and a coupling member positioned adjacent a second surgical sleeve. In one embodiment, at least one of the drive member and the coupling member can be releasably engaged to an actuation mechanism. In one aspect, the actuation mechanism can include a floating and/or auto-locking pivot point thereby allowing a user to quickly and easily position the manipulation device relative to the adjacent surgical sleeves. Additionally, a method of manipulating spinal constructs is also provided.

21 Claims, 20 Drawing Sheets

(56) References Cited

U.S. PATENT DOCUMENTS

| | | |
|---|---|---|
| 2006/0036254 A1* | 2/2006 | Lim ................ A61B 17/7086 606/86 R |
| 2006/0122597 A1 | 6/2006 | Jones et al. |
| 2006/0166535 A1 | 7/2006 | Brumfield et al. |
| 2006/0195114 A1 | 8/2006 | Bertagnoli |
| 2006/0217735 A1 | 9/2006 | MacDonald et al. |
| 2006/0235427 A1 | 10/2006 | Thomas et al. |
| 2009/0182345 A1 | 7/2009 | Medoff et al. |
| 2010/0004695 A1 | 1/2010 | Stad et al. |

* cited by examiner

SYSTEM AND METHOD FOR MANIPULATING A SPINAL CONSTRUCT

RELATED APPLICATION(S)

The present application is a divisional of U.S. application Ser. No. 12/168,455, filed Jul. 7, 2008, entitled "System and Method for Manipulating a Spinal Construct," the entirety of which is incorporated herein by reference.

FIELD

The present disclosure relates to manipulation of spinal constructs.

BACKGROUND

Spinal fixation devices and systems are used to align and/or fix a desired relationship between adjacent vertebral bodies. Such devices typically include a spinal fixation element, such as a relatively rigid fixation rod or plate, that is coupled to adjacent vertebrae by attaching the element to various anchoring devices, such as hooks, bolts, wires, or screws. The fixation element can have a predetermined contour that has been designed according to the properties of the target implantation site, and once installed, the fixation element can hold the vertebrae in a desired spatial relationship, either until desired healing or spinal fusion has taken place, or for some longer period of time.

In use, a spinal fixation element can be anchored to specific portions of a vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screw assemblies typically include a threaded shank capable of being positioned within a vertebra, and a head portion having a fixation rod-receiving element, usually in the form of a U-shaped recess. A set-screw, plug, or similar type of closure mechanism can be used to secure the fixation element, e.g., a spinal rod, into the rod-receiving head of the pedicle screw.

Often, such fixation procedures will require some degree of manipulation of the spinal construct(s) in order to properly position the fixation element and/or to achieve the desired therapeutic effect. Typically, such manipulation includes compression or distraction of the construct. However, these manipulation steps can be problematic as the working area tends to be crowded and the required instrumentation can be difficult to position, adjust, and/or maintain at a desired location.

SUMMARY

A system for manipulating a spinal construct is provided. More specifically, the system includes a manipulation device which is configured to enhance a user's ability to accurately and efficiently couple the device to adjacent surgical sleeves extending from a spinal construct. For example, the manipulation device can include various modular components thereby providing greater flexibility and versatility in engaging the device to the adjacent sleeves which may not be in an ideal position for coupling. Also, the manipulation device can include a floating and auto-locking pivot point thereby allowing the user to quickly and easily change the arc of rotation of those members of the device which are coupled and/or placed into communication with the adjacent surgical sleeves. Thus, the presently disclosed system provides spinal surgeons with a powerful instrument and system for performing both minimally invasive surgery and open surgical procedures.

Various aspects of such a manipulation system and device are provided. In one such aspect, the spinal manipulation device includes a drive member having an elongate shaft which is sized and configured to be disposed within an inner lumen of a first surgical sleeve extending from a first vertebra. Additionally, the device includes a coupling member being sized and configured to maintain a spatial relationship relative to a second surgical sleeve extending from a second vertebra as the coupling member pivots relative to the drive member. The device can also include an actuation mechanism effective to pivot the drive member relative to the coupling member wherein at least one of the drive member and the coupling member are releasably engaged to the actuation mechanism.

As will be described in detail below, the coupling member can be placed into communication with the second surgical sleeve in various manners. For example, in one such embodiment the coupling member can be sized and configured to be positioned immediately above the second surgical sleeve so as to receive the driver. For example, in such an embodiment the coupling element includes a cap-shaped element having a central bore. In another embodiment, the coupling member includes a semi-circular extension which is sized and configured to extend along and adjacent to an outer portion of the second surgical sleeve. In yet another embodiment, the coupling member can include a retractable element configured to move from a retracted position to an extended position such that in the retractable element can be positioned above the second surgical sleeve when in the retracted position, and the retractable element can extend along a length of the second surgical sleeve when in the extended position.

The actuation mechanism can also be configured in various manners. For example, in one embodiment, the actuation mechanism can include a first handle element pivotally coupled to a second handle element. As will be described, the actuation mechanism can also be configured to enable either compression or distraction of the spinal construct. For example, in the case of compression, a distal portion of the first handle element is configured to engage the drive member, and a distal portion of the second handle element is configured to engage the coupling member thereby allowing the drive member and the coupling member to move towards one another as the first handle element pivots towards the second handle element. In the case of distraction, a distal portion of the first handle element is configured to engage the coupling member, and a distal portion of the second handle element is configured to engage the drive member thereby allowing the drive member and the coupling member to pivot away from one another as the first handle element pivots towards the second handle element.

The actuation mechanism can also include various other features. For example, the actuation mechanism can include a locking mechanism capable of locking the position of the drive member relative to the coupling member. More specifically, the actuation mechanism can include a locking mechanism which includes a locking lever extending from a proximal end of the second handle member and configured to releasably engage a proximal end of the first handle element.

In another aspect, a spinal manipulation device is provided which includes a drive member having an elongate shaft which is sized and configured to be disposed within an inner lumen of a first surgical sleeve extending from a first vertebra. Additionally, the device includes a coupling member being sized and configured to maintain a spatial relationship relative to a second surgical sleeve extending from a second vertebra as the coupling member pivots relative to the drive member.

The device also includes an actuation mechanism effective to pivot the drive member relative to the coupling member. As will be described, the actuation mechanism can include first and second handles joined at a selectively movable pivot that allows selective lateral positioning of the drive member relative to the coupling member.

The selectively movable pivot can be provided in various manners. For example, the movable pivot can include an elongate slot formed on the first handle that is sized and configured to receive a pin extending from the second handle element. Additionally, the elongate slot can include a plurality of seating areas which can be sized and configured to seat and retain the pin (or some element coupled to or in communication with the pin) to create a desired pivot point.

In another aspect, a spinal manipulation device is provided which includes a drive member having an elongate shaft which is sized and configured to be disposed within an inner lumen of a first surgical sleeve extending from a first vertebra, and also including a coupling member having a retractable element configured to move between a retracted position and an extended position. Thus, the coupling member can be configured to reside above a second surgical sleeve extending from a second vertebra thereby allowing the retractable member to enter an inner lumen of the second surgical sleeve as the retractable member moves from the retracted position to the extended position. Additionally, the device can include an actuation mechanism effective to pivot the drive member relative to the coupling member. In one embodiment, the actuation mechanism can include first and second handles joined at a selectively movable pivot that allows selective lateral positioning of the drive member relative to the coupling member.

Similar to other aspects described above, the movable pivot can be configured in various manners. For example, the movable pivot can include an elongate slot formed on the first handle that is sized and configured to receive a pin extending from the second handle element. The pin can be in communication with an engagement lever having at least one seating area configured to engage a corresponding seating area(s) formed along the elongate slot. In one embodiment, the seating area of the engagement lever can be biased away from the corresponding seating area of the elongate slot in the absence of an actuation force, and configured to move towards and into contact with the corresponding seating area of the elongate slot during application of the actuation force.

Various aspects of a method of manipulating a spinal construct are also provided. In one such aspect, the method includes disposing an elongate shaft of a drive member within an inner lumen of a first surgical sleeve extending from a first vertebra of a spinal construct, and positioning a coupling member adjacent a second surgical sleeve extending from a second vertebra of the spinal construct. Next, the method includes engaging at least one of the drive member and the coupling member to an actuation mechanism. The method also includes disposing a driver within an inner lumen of the second surgical sleeve, and providing an actuation force to the actuation mechanism to pivot the drive member relative to the coupling member to provide a desired manipulation force to the spinal construct. In one example, applying the actuation force can include squeezing a second handle element of the actuation mechanism towards the first handle element of the actuation mechanism.

As will be described, the steps of the presently disclosed method can be performed in a minimally invasive surgical procedure, or as an open procedure.

BRIEF DESCRIPTION OF THE DRAWINGS

The present disclosure will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

The presently disclosed system and method facilitates spinal fixation procedures by enhancing a user's control over the instrumentation required to compress and/or distract a spinal construct. For example, the system is generally used with first and second surgical sleeves that extend from adjacent vertebrae of a spinal construct with each sleeve being releasably engaged to a rod-receiving head of a bone anchor. In use, a fixation rod can be secured to the receiving head of the first bone anchor coupled to the first surgical sleeve ("the locked sleeve") by use of a set screw, and the fixation rod can remain unsecured to the receiving head of the second bone anchor coupled to the second surgical sleeve ("the unlocked sleeve"). The system includes a spinal manipulation device which can readily couple to the adjacent surgical sleeves. More specifically, the manipulation device can include a first member (i.e., a drive member) capable of being disposed within an inner lumen of the locked sleeve, and can also include a second member (i.e., a coupling member) capable of being positioned adjacent the unlocked sleeve. Each member can be coupled to an actuation mechanism thereby allowing the members to pivot relative to one another. Various embodiments of the device are provided herein so as to facilitate the positioning of these members relative to the surgical sleeves. In one such embodiment, at least one of these members (or both) can be releasably engaged to the actuation mechanism. In another embodiment, the actuation mechanism can be effective to pivot the drive member relative to the coupling member wherein the actuation mechanism includes first and second handles joined at a selectively movable pivot that allows selective lateral positioning of the drive member relative to the coupling member. The system can also include a driver disposed within an inner lumen of the unlocked sleeve. In use, as a user supplies a force to the unlocked sleeve, a pivot point defined by the actuation mechanism can serve as a fulcrum thereby optimizing the amount of force delivered to the spinal construct.

Figure 1A:
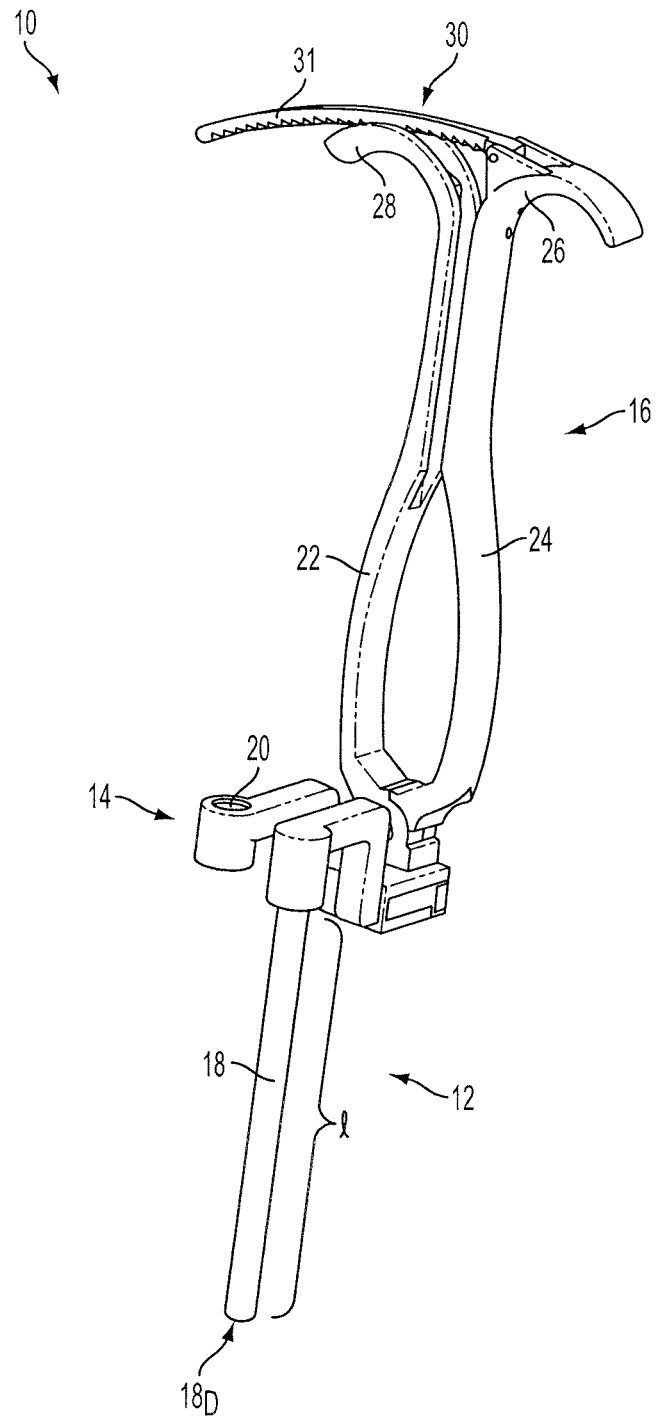
FIG. 1A is a perspective view of an exemplary embodiment of a manipulation device.
Figure 1B:
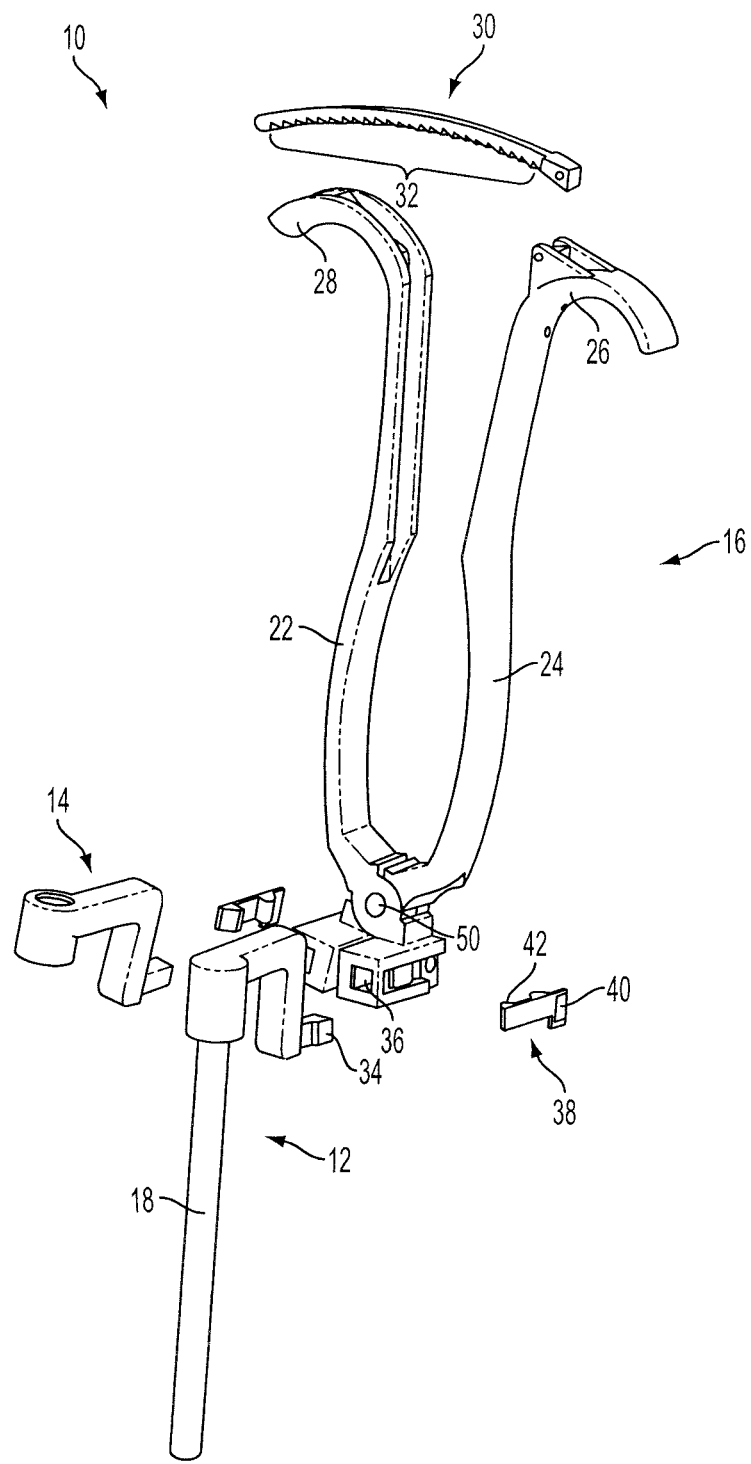
FIG. 1B is an exploded view of the manipulation device of FIG. 1A.

Various embodiments of such a manipulation device are within the spirit and scope of the present disclosure. FIGS. 1A and 1B provide an exemplary embodiment of a such a manipulation device 10 having a drive member 12 and a coupling member 14 appended to an actuation mechanism 16. As indicated above, the drive member 12 can be sized and configured to be disposed within an inner lumen of a locked sleeve 52, and the coupling member 14 can be sized and configured to be positioned adjacent an unlocked sleeve 54 (see FIG. 4A). In one embodiment, one or both of the drive member 12 and the coupling member 14 can be integrally formed with the device. In an exemplary embodiment, however, one or both of the drive member 12 and the coupling member 14 can be releasably engaged to the actuation mechanism 16. Thus, the user can couple the drive member 12 relative to the locked sleeve 52 and can independently position the coupling member 14 relative to the unlocked sleeve 54 without being constrained by one another. Once these members 12, 14 are positioned as desired and securely coupled to the actuation mechanism 16, a driver 150 (see FIGS. 7C-7D) can be disposed within an inner lumen of the unlocked sleeve 54 and an actuation force can be supplied to the actuation mechanism 16 thereby utilizing the pivot point as a fulcrum in optimizing an amount of force delivered to the spinal construct. The various components of the manipulation device 10 are now described in detail.

As indicated, the manipulation device 10 includes a drive member 12 having an elongate shaft 18 which is sized and configured to be disposed within the inner lumen of the locked sleeve 52. Those skilled in the art will appreciate that various dimensions of such a drive member 12 are within the spirit and scope of the present disclosure. For example, in an exemplary embodiment, the elongate shaft 18 of the drive member 12 will have a length/slightly longer than a length of the locked sleeve 52 thereby allowing a distal portion of the elongate shaft $18_D$ to be positioned adjacent the tightened set screw (not shown) of the bone anchor when the shaft 18 is disposed within the locked sleeve 52. Additionally, a diameter of the elongate shaft 18 can be selected so as to be slightly less than an inner diameter of the locked sleeve 52 thereby optimizing the stability and strength of the drive member 12 during manipulation of the spinal construct.

Figure 2:
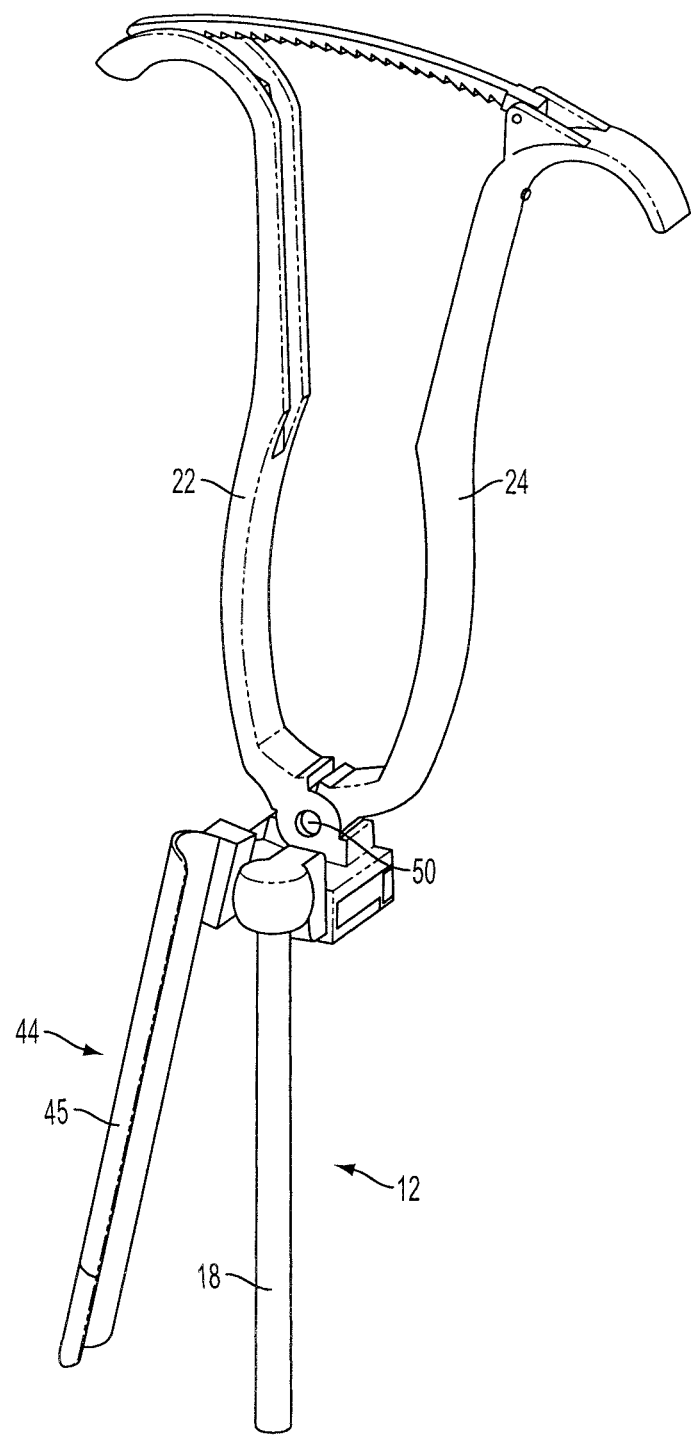
FIG. 2 is a perspective view of another exemplary embodiment of a manipulation device.

The manipulation device 10 also includes a coupling member 14 that can be positioned adjacent the unlocked sleeve 54. In general, the coupling member 14 is any such member capable of maintaining a spatial relationship with the unlocked sleeve 54 during application of the manipulation force while also pivoting relative to the drive member 12. As detailed below, maintaining this spatial relationship with the unlocked sleeve 54 while pivoting relative to the drive member 12 provides a fulcrum during application of a manipulation force to the adjacent sleeves (see FIGS. 7C-7D). Thus, various embodiments of such a coupling member are within the spirit and scope of the present disclosure. For example, FIGS. 1A-1B provide an exemplary embodiment of a cap-shaped coupling member 14 which is sized and configured to reside immediately above (see FIG. 4B) a proximal portion of the unlocked sleeve 54. Additionally, the cap-shaped member 14 can include a central bore 20 which is sized and configured to receive the driver 150 as the driver 150 is disposed within the unlocked sleeve 54 (again, see FIGS. 7C-7D). In other embodiments, the coupling member can include an elongate sleeve member (not shown) which can be disposed within the unlocked sleeve and can also be configured to receive the driver. FIG. 2 provides yet another exemplary embodiment of a coupling member 44 wherein the member 44 is a semi-circular extension 45 sized and configured to extend along an inner or outer portion of the unlocked sleeve 54. In yet another embodiment, the coupling member can be a cap-shaped element which is sized and configured to receive a proximal portion of the unlocked sleeve 54.

Figure 3A:
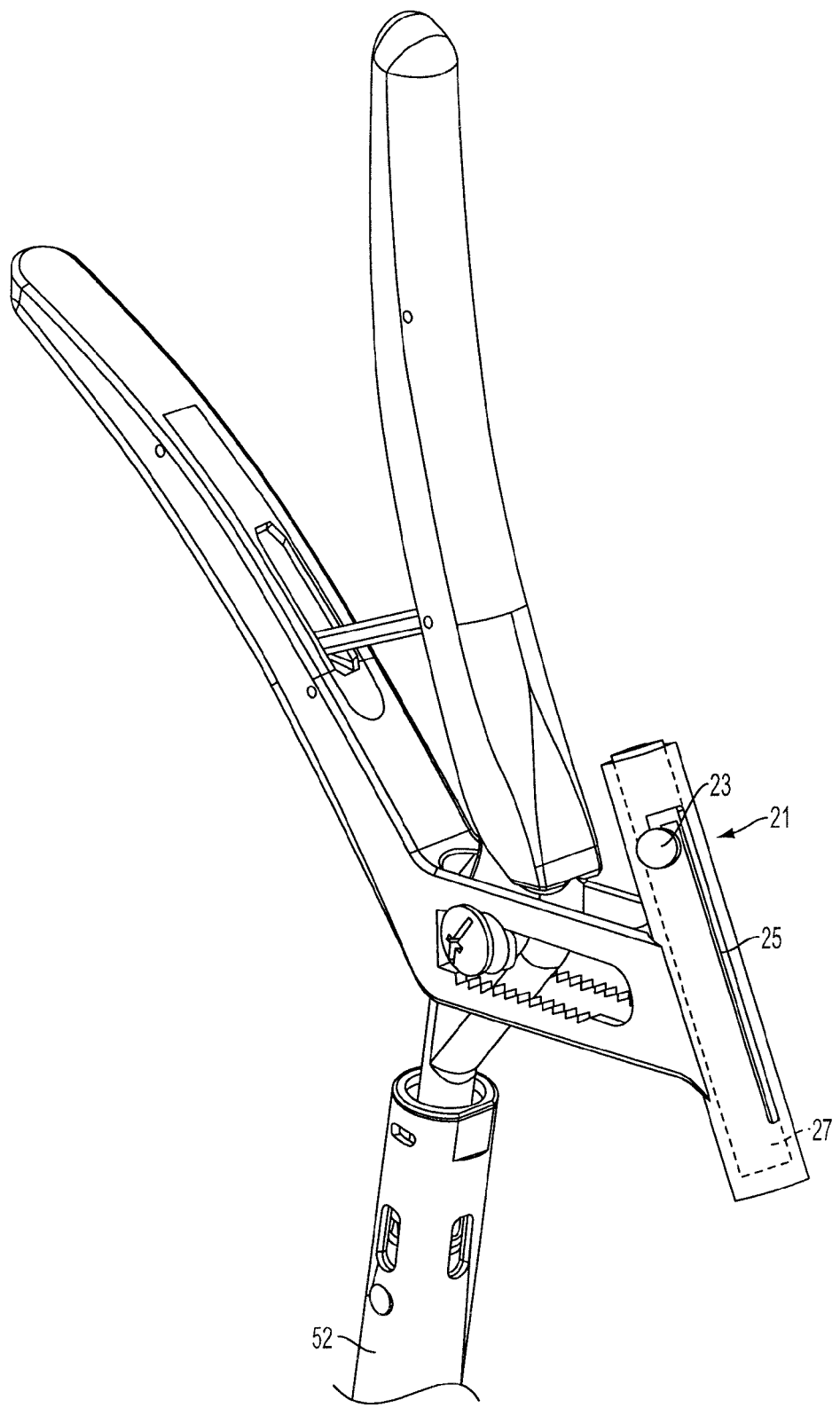
FIG. 3A is a perspective view of another embodiment of a manipulation device.
Figure 3B:
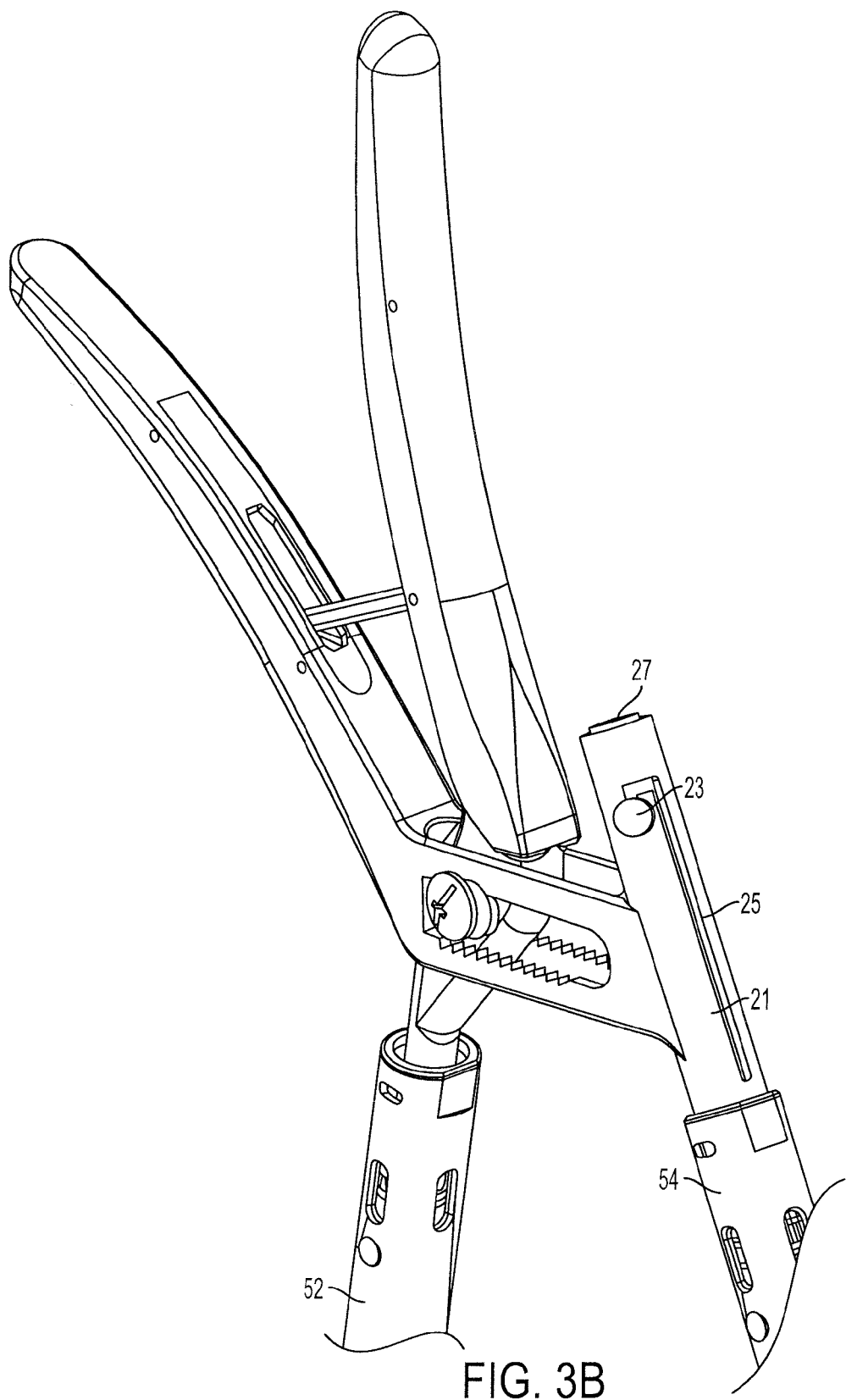
FIG. 3B is another perspective view of the embodiment of FIG. 3A.
Figure 3C:
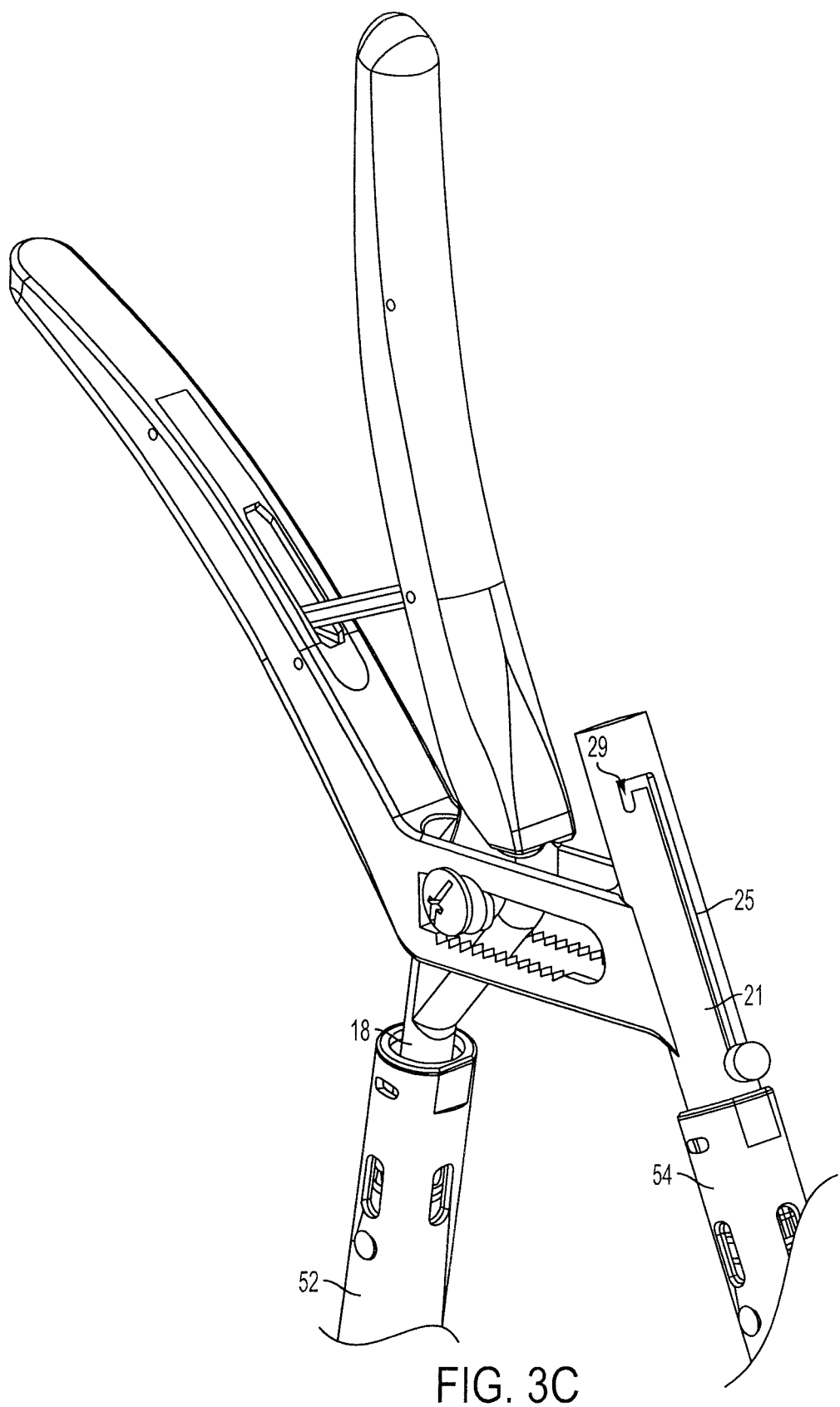
FIG. 3C is yet another perspective view of the embodiment of FIG. 3A.

In another embodiment, as shown in FIGS. 3A-3C, the device can include a coupling member 21 having a retractable element 27 capable of moving between a retracted position (shown in FIGS. 3A-3B) and an extended position (shown in FIG. 3C). More specifically, as shown in FIG. 3A, the coupling member 21 can be a cylindrically-shaped member having an inner lumen which is sized so as to receive a retractable element 27 (e.g., a rod). The retractable element 27 can be engaged to the coupling member 21 such that the retractable element 27 can move between a retracted position and an extended position. That is, in a retracted position, the retractable element 27 can be substantially housed within the inner lumen of the coupling member 21 thereby facilitating positioning of the coupling member 21 relative to a second surgical sleeve 54. Once the coupling member 21 is positioned as desired (shown in FIG. 3B), the retractable element 27 can be moved from the retracted position to the extended position. In the extended position (shown in FIG. 3C), the retractable element 27 can move distally thereby exiting the inner lumen of the coupling member 21 and assuming a desired orientation relative to the second surgical sleeve 54. For example, as shown, in moving from the retracted position to the extended position, the retractable element 27 can extend into an inner lumen of the second surgical sleeve. In other embodiments (not shown), the retractable element 27 can extend along an outer portion of the second surgical sleeve 54 as the retractable element 27 moves from the retracted position to the extended position.

Those skilled in the art will appreciate that the retractable element 27 can be retractably engaged to the coupling member 21 in various manners. For example, as shown in FIGS. 3A-3C, the retractable element 27 can include a proximal end having a knob element 23 extending perpendicularly out therefrom. Additionally, the coupling member 21 can include a slot 25 configured to allow the knob 23 (and therefore the retractable element 27) to extend lengthwise relative to the coupling member 21. Additionally, a notch 29 (FIG. 3C) can be formed at a proximal end of the slot 25 thereby allowing the retractable element 27 to be retained in the retracted position as desired.

Figure 4A:
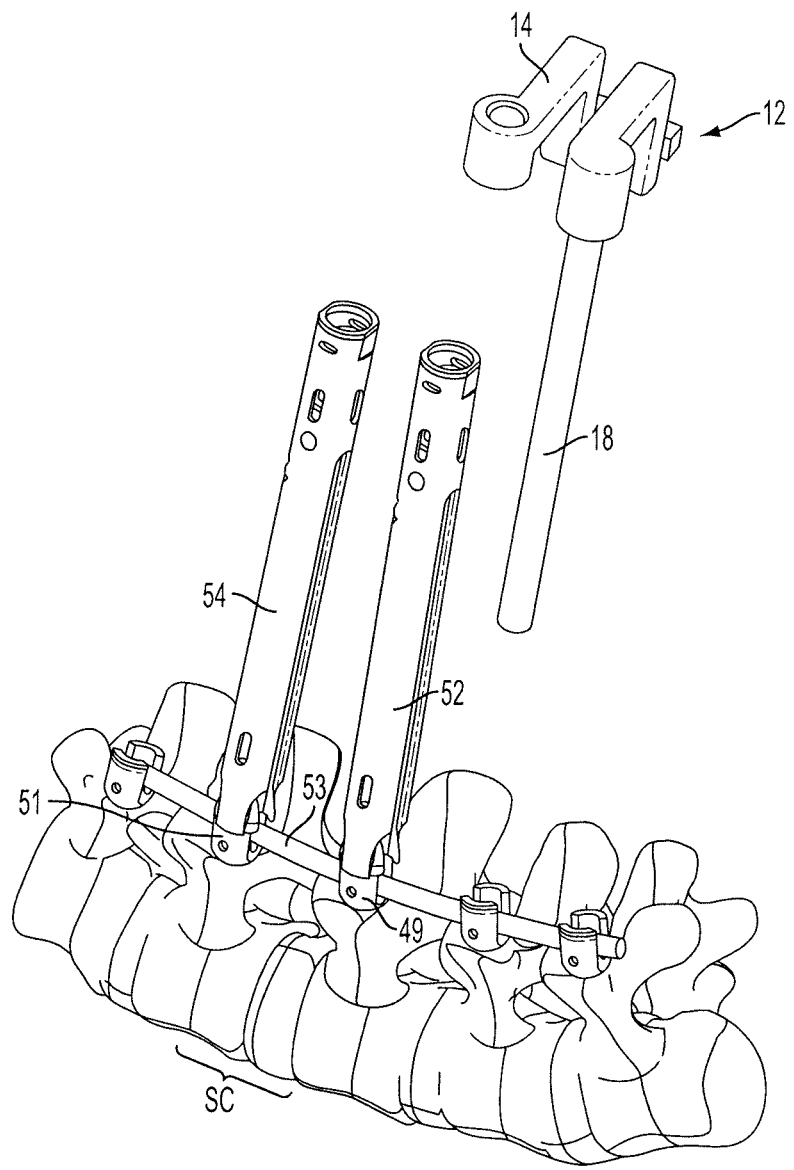
FIG. 4A is a representation of a modular drive member and a modular coupling member of the manipulation device of FIG. 1A.
Figure 4B:
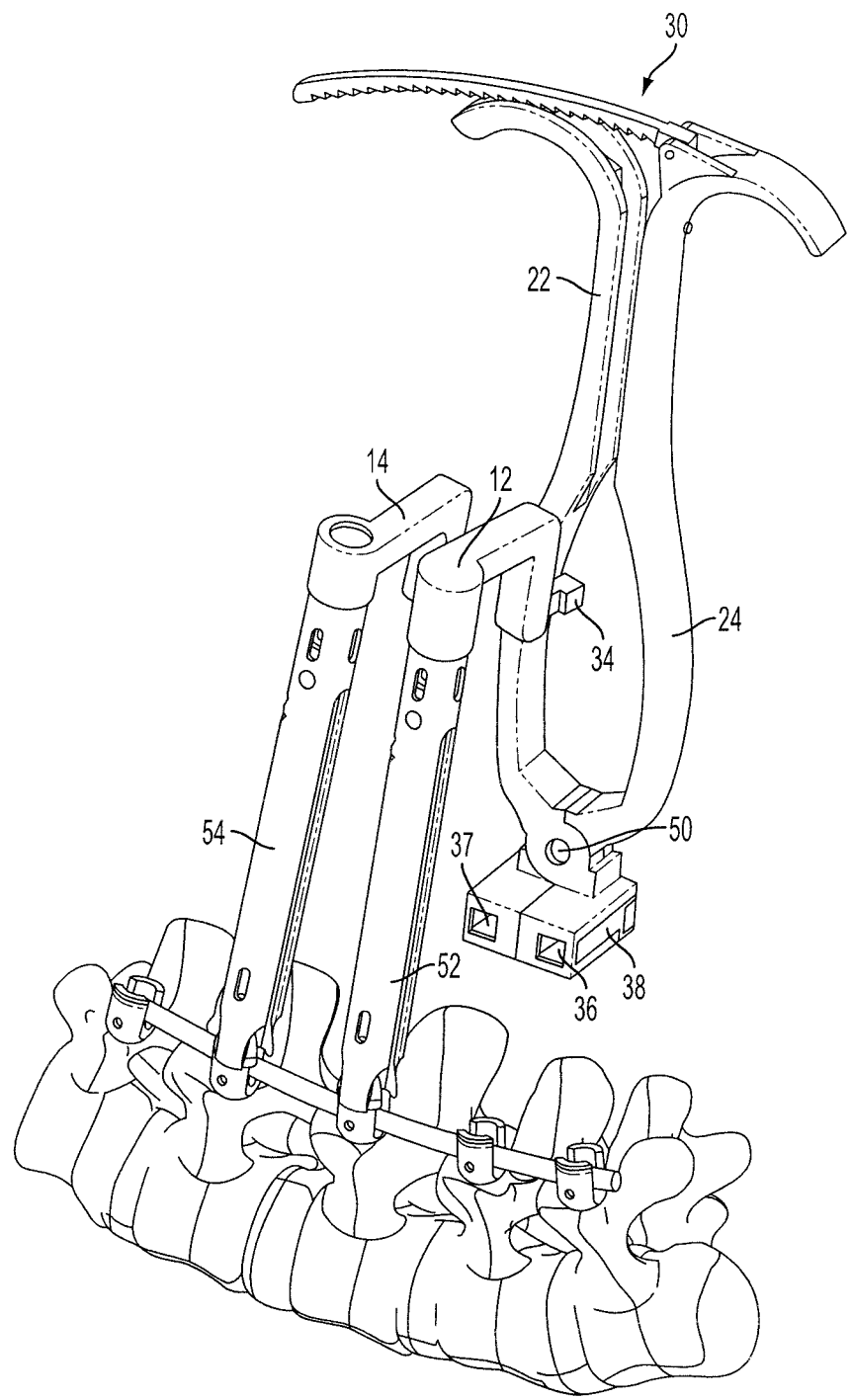
FIG. 4B is a representation of the modular drive member positioned relative to a first surgical sleeve and the modular coupling member positioned relative to an adjacent surgical sleeve.
Figure 4C:
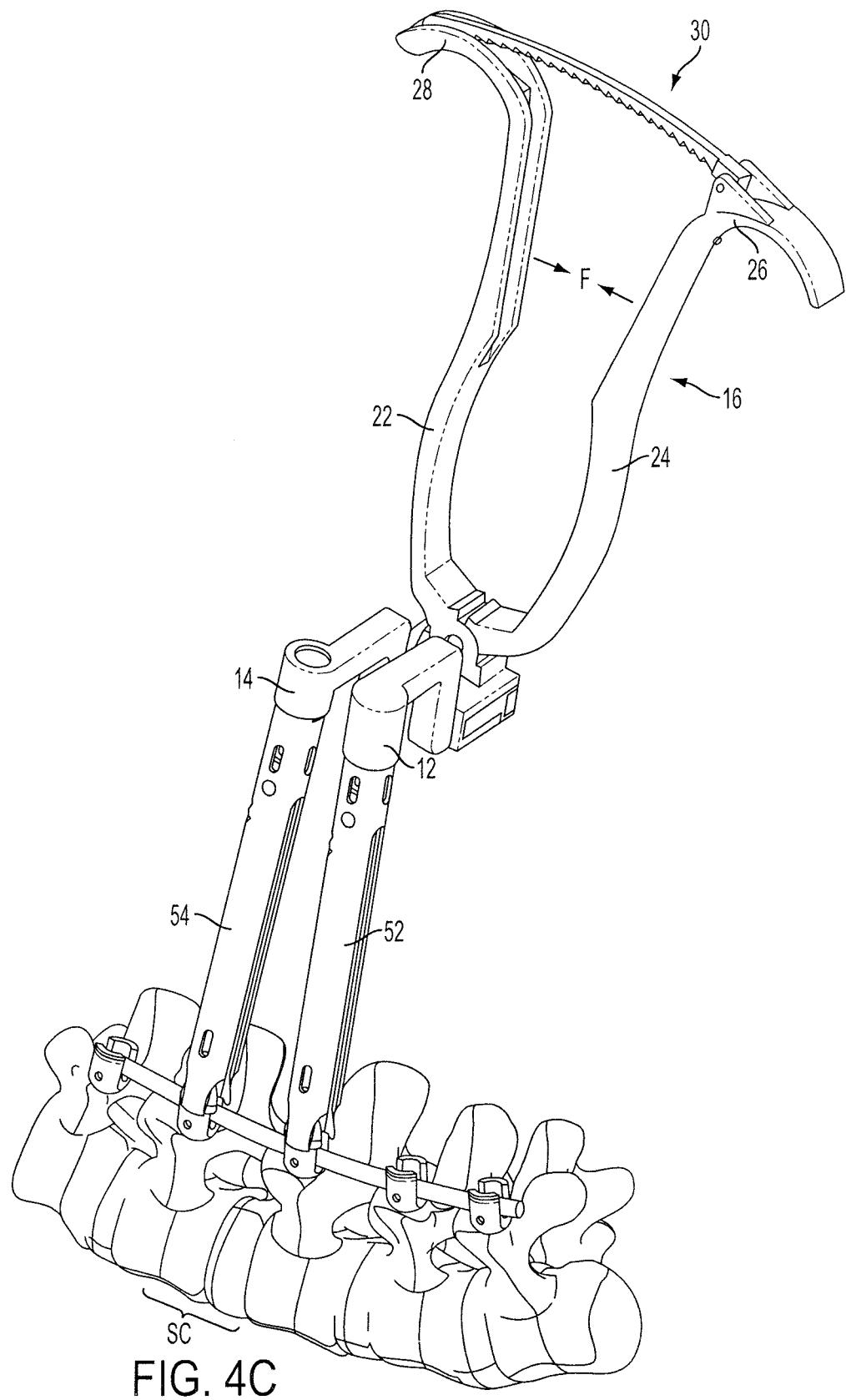
FIG. 4C is a representation of an actuation mechanism being releasably engaged to the drive member and the coupling member.
Figure 4D:
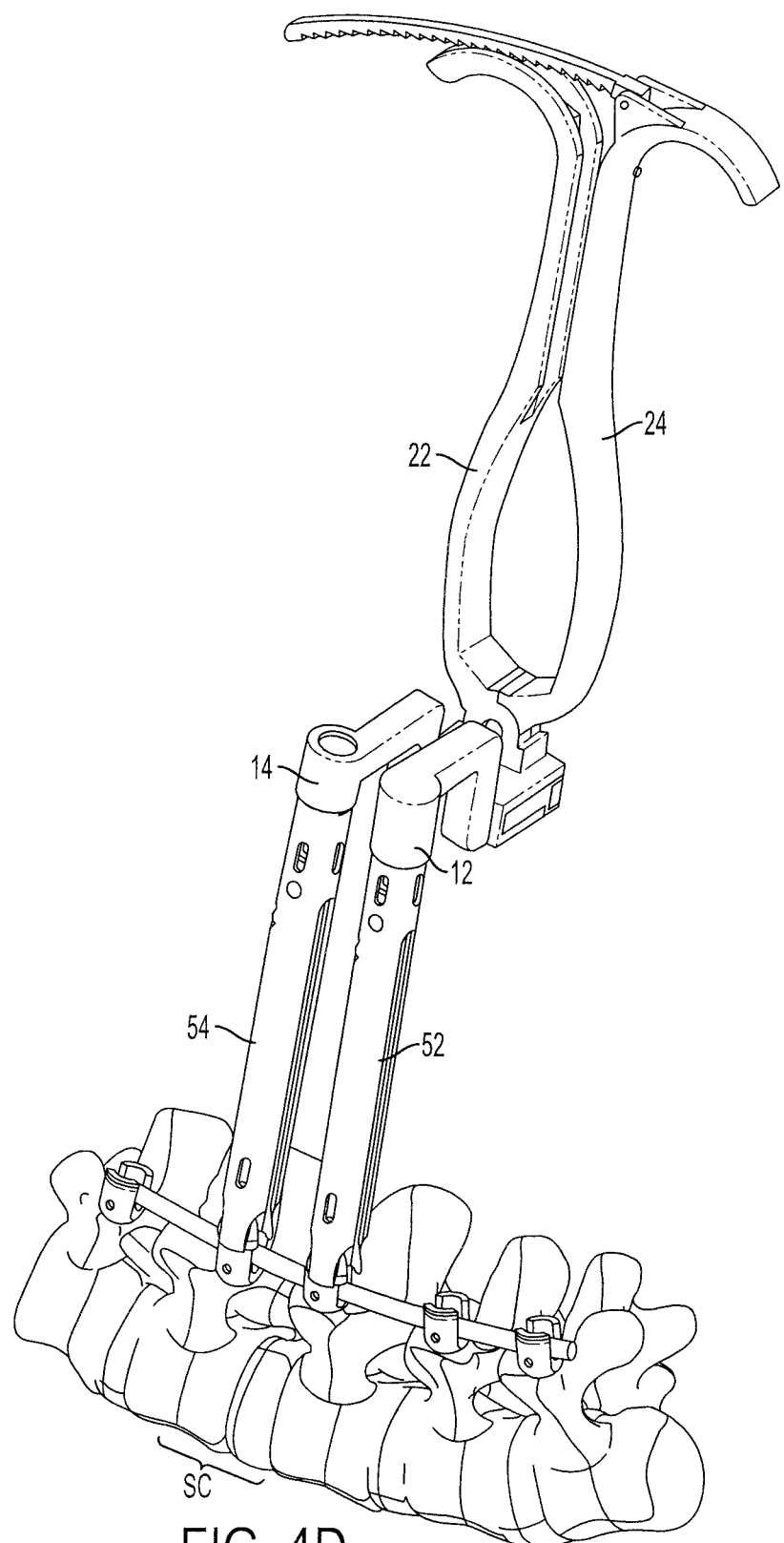
FIG. 4D is a representation of the actuation mechanism following compression of the spinal construct.
Figure 5A:
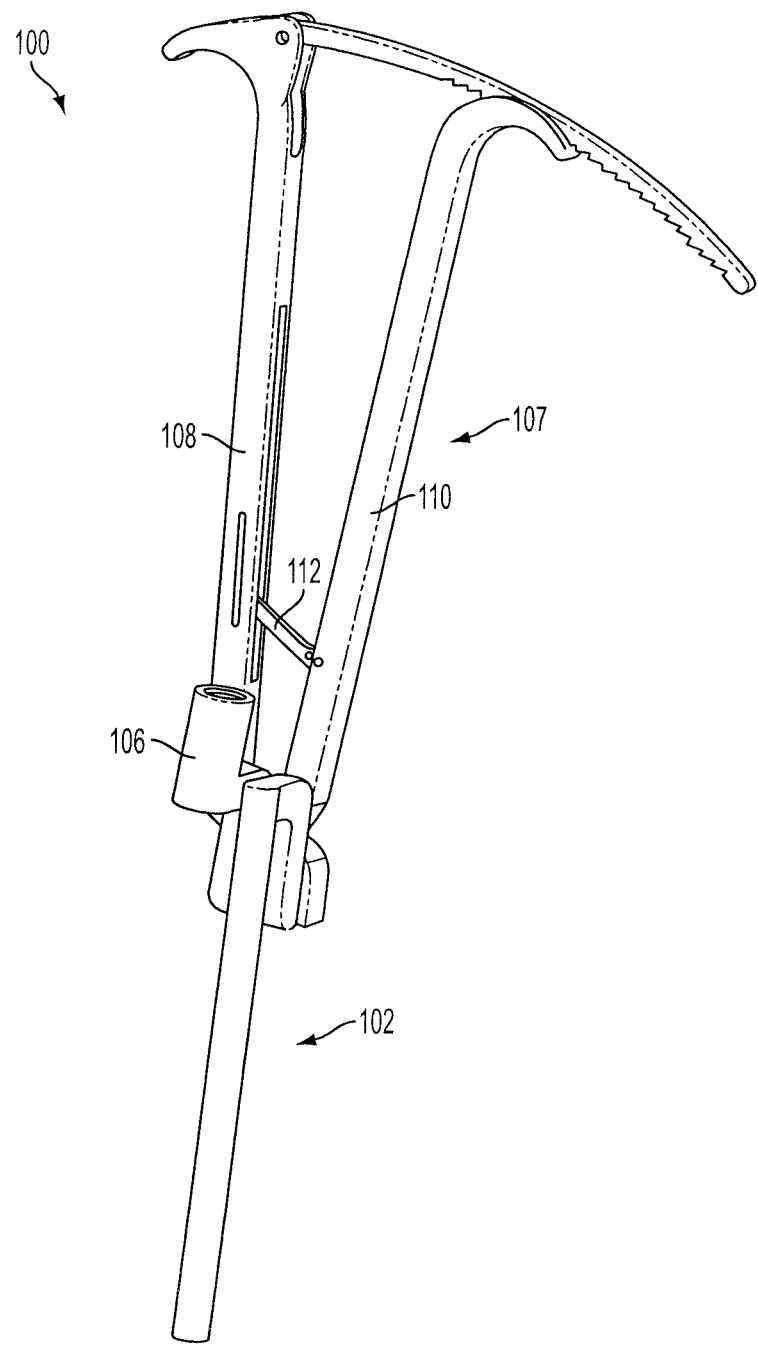
FIG. 5A is a perspective view of another exemplary embodiment of a manipulation device having a floating, auto-locking pivot point.
Figure 5B:
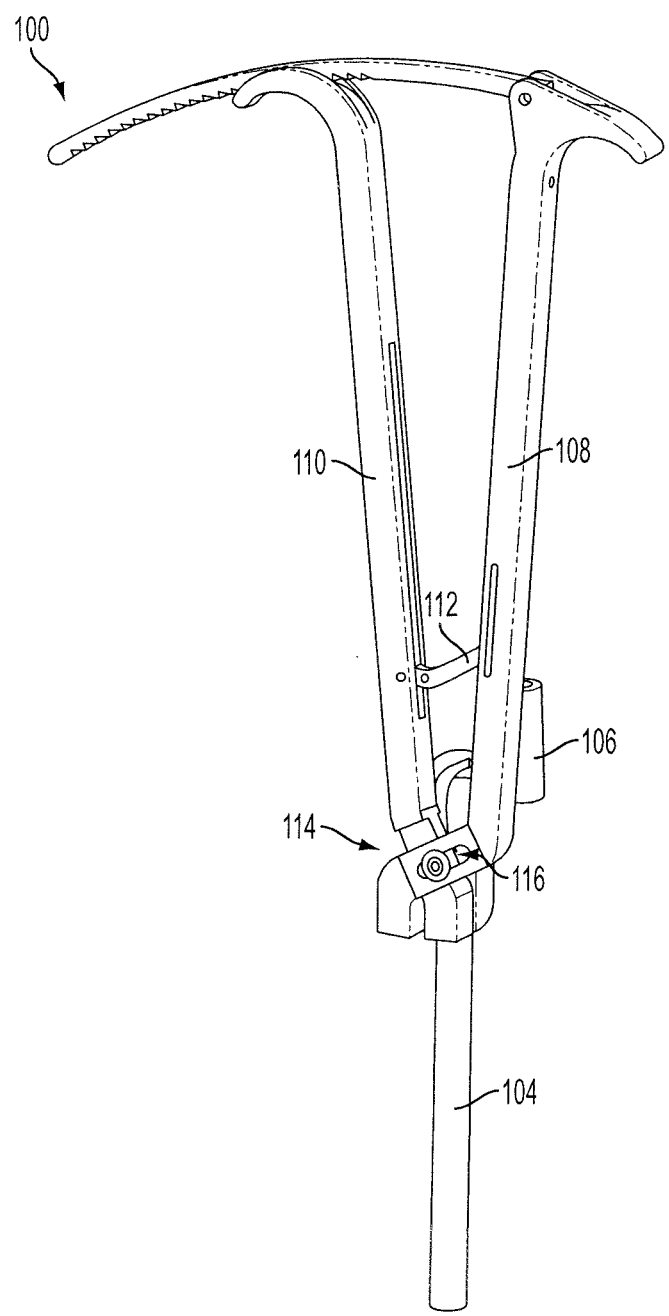
FIG. 5B is an alternative view of the manipulation device of FIG. 5A.
Figure 5C:
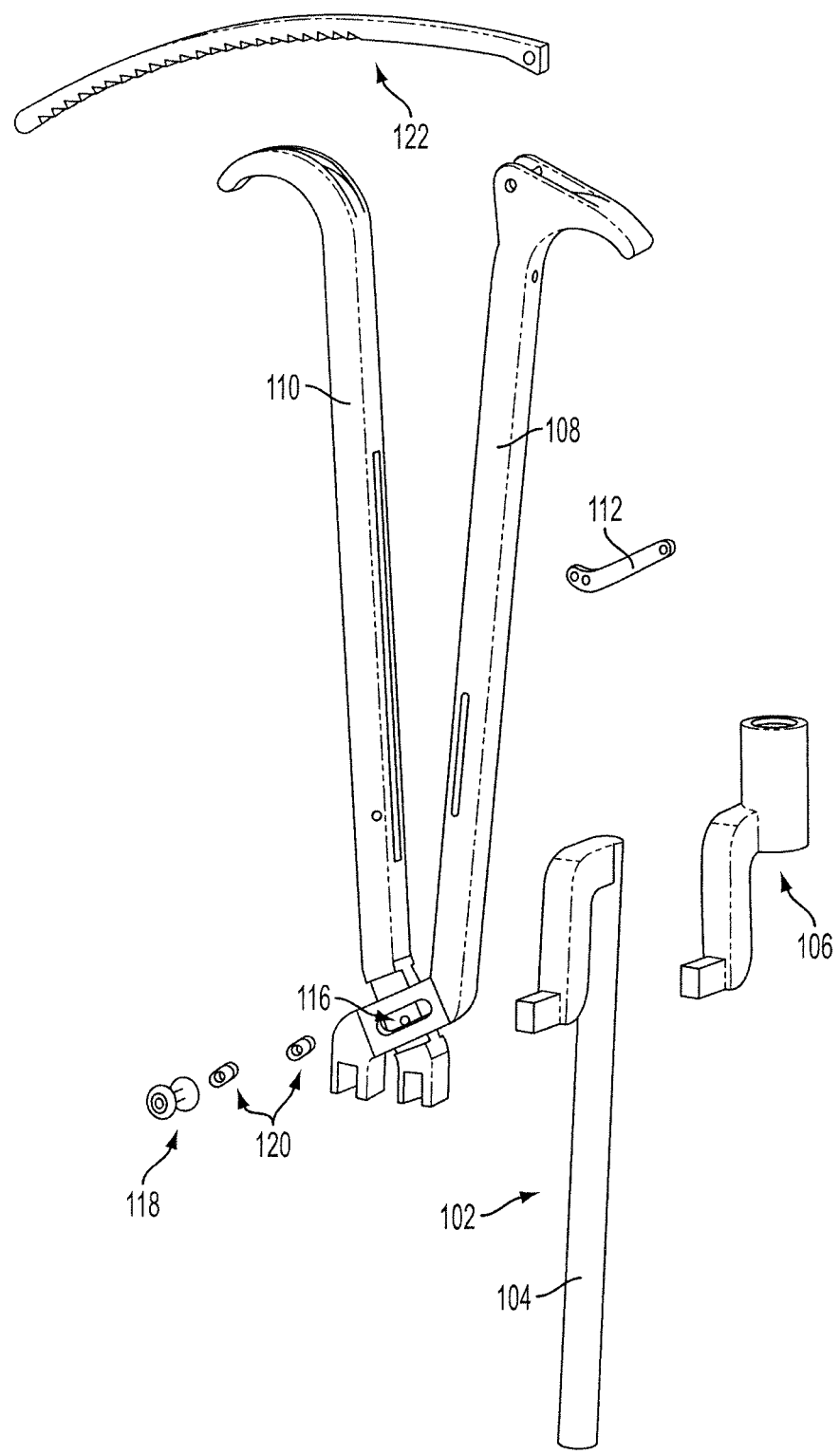
FIG. 5C is an exploded view of the manipulation device of FIG. 5A.
Figure 5D:
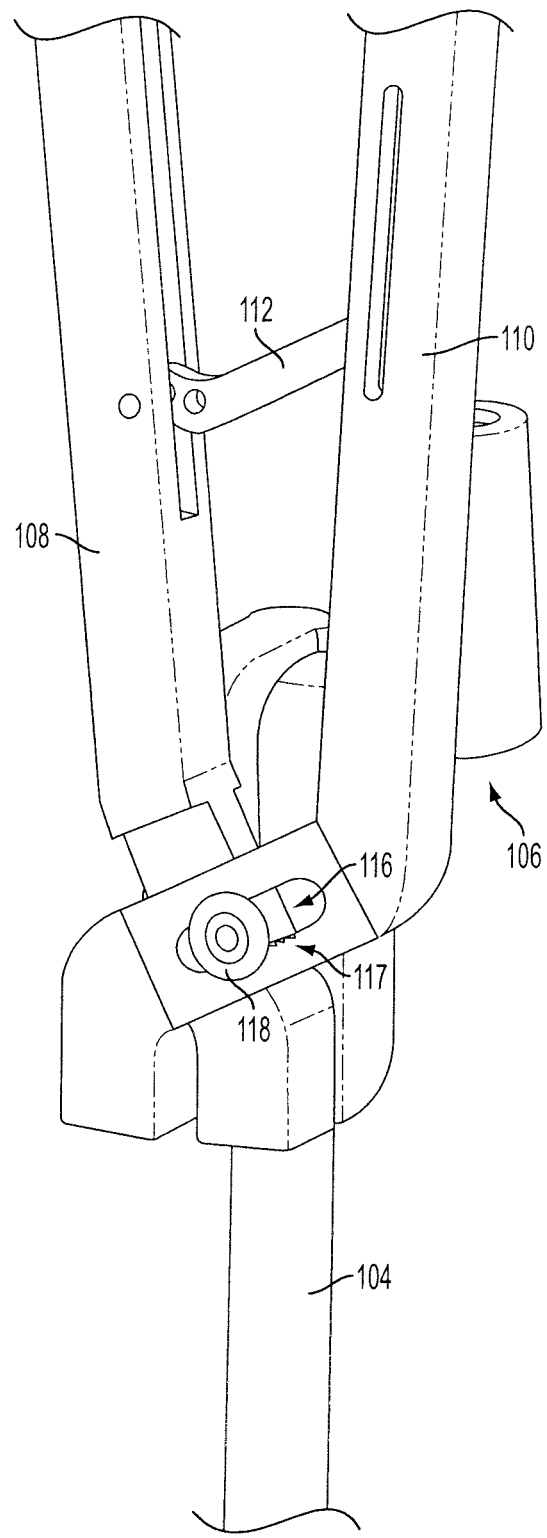
FIG. 5D is an enlarged view of the floating, auto-locking pivot point of FIG. 5A.

In enhancing versatility and effectiveness, the manipulation device 10 can be configured as a modular device in that one or both of the drive member and/or coupling member can be releasably engaged to an actuation mechanism. Thus, as shown in FIGS. 4A-4C, the user can position the drive member 12 in communication with the locked sleeve 52 and also position the coupling member 14 in communication with the unlocked sleeve 54 without being constrained or limited by one another. Such modularity can provide significant benefits when working in an overcrowded treatment site (as is often the case in spinal surgery) and in those situations where the surgical sleeves 52, 54 are positioned awkwardly relative to one another thereby presenting difficulty in coupling the first and second members 12, 14 to the sleeves 52, 54.

As will be apparent to those skilled in the art, the drive member 12 and/or the coupling member 14 can be configured in various manners so as to allow these members 12, 14 to releasably engage an actuation mechanism 16 (which is described in detail below). FIGS. 1B and 4B show an exemplary embodiment wherein a proximal portion of each of the drive member 12 and the coupling member 14 includes a protrusion 34 (protrusion of coupling member 14 not clearly shown) which is sized and configured to be inserted into corresponding openings 36, 37 at a distal portion of the actuation mechanism 16. Once positioned as such, a biased lever 38 (e.g., spring biased) formed adjacent each opening 36, 37 (lever adjacent opening 37 not clearly shown) can be configured to receive the protrusion 34 thereby securely engaging each member 12, 14 to the actuation mechanism 16. To release the member 12, 14 from the actuation mechanism 16, a portion 38 of the lever 38 can be compressed thereby disengaging a corresponding protrusion 42 of the lever 38 from the protrusion 34 of the member thereby releasing the member 12, 14 from the actuation mechanism 16. Again, this embodiment is merely an example and any such mechanism for releasably engaging the drive member 12 and/or the coupling member 14 to the actuation mechanism 16 is within the spirit and scope of the present disclosure.

As mentioned previously, the device includes an actuation mechanism 16 which is effective to pivot the drive member 12 relative to the coupling member 14 at a pivot point. As detailed further below, this pivot point can serve as a fulcrum during application of a manipulation force on the spinal construct. As will be apparent to those skilled in the art, various such actuation mechanisms 16 are within the spirit and scope of the present disclosure. For example, FIGS. 1A, 1B, and 2 provide an exemplary embodiment of an actuation mechanism 16 that includes a first handle element 22 pivotally coupled to a second handle element 24 at the pivot point 50. As shown, the actuation mechanism 16 can engage the above-described drive member 12 and the coupling member 14 at a location distal of the pivot point 50. In use, the application mechanism 16 can translate a force along the elongate shaft 18 of the drive member 12 disposed within the locked sleeve 52. During application of such a force, if desired, a driver 150 (FIGS. 7C-7D) disposed within the unlocked sleeve 54 can exert an additional force on the spinal construct. In coupling these forces, the driver 150 can also utilize the pivot point 50 of the actuation mechanism 16 as a fulcrum, and the first handle element 22 of the actuation mechanism 16 can be squeezed towards the second handle element 24 of the mechanism 16 thereby focusing the forces on the spinal construct to provide the desired manipulation.

The actuation mechanism 16 can be configured in various manners such that squeezing the first handle element 22 towards the second handle element 24 allows the drive member 12 and coupling member 14 to move towards one another (in the case of compression) or away from one another (in the case of distraction), as desired. More specifically, referring to FIG. 1A-1B, in the case of compression, the actuation mechanism 16 can be configured in a scissors-like configuration in which the first handle element 22 crosses over the second handle element 24 at the pivot point 50 thereby allowing the drive member 12 and the coupling member 14 to pivot towards one another as the handle elements 22, 24 are squeezed towards one another. Alternatively, in the case of distraction (not shown), the first and second handle elements 22, 24 can be coupled in a non-scissors-like configuration such that the elements 22, 24 do not cross one another at the pivot point 50. Thus, in such an embodiment, the drive member 12 is engaged to the second handle member 24 and the coupling member 14 is engaged to the first handle element 22. Thus, squeezing the first and second handle elements 22, 24 towards one another moves the drive member 12 away from the coupling member 14.

The actuation mechanism 16 can also include various additional features. For example, the actuation mechanism 16 can include some type of locking mechanism configured to maintain the position of the first handle element 22 relative to the second handle element 24. Those skilled in the art will appreciate that virtually any type of locking mechanism can be incorporated into the actuation mechanism. For example, as shown in FIGS. 1A-1B, the locking mechanism 30 can be a locking lever 31 extending from a proximal end 26 of a second handle element 24 and configured to releasably engage a proximal end 28 of the first handle element 22. As will be appreciated by those skilled in the art, the locking lever 31 and/or the proximal end 28 of the first handle element 28 can be configured in various manners so as to allow the locking lever 31 to releasably engage the proximal end 28 of the first handle portion 22. Further, the locking mechanism 30 can be configured to allow for the first and second handle members 22, 24 to be locked relative to one another at any of a plurality of positions. For example, as shown in FIG. 1B, the locking lever 31 can include a plurality of retro-grade teeth 32 extending along a length thereof wherein each tooth 32 can be capable of releasably engaging the proximal end 28 of the first handle element 22. Thus, the locking mechanism 30 can allow for incremental compression or distraction of the spinal construct as the proximal end 28 of the first handle element 22 incrementally engages successive teeth 32 of the locking lever 31.

In addition to the embodiments described above, the manipulation device can be configured in various alternative or additional manners so as to facilitate coupling of the device to the adjacent surgical sleeves. For example, in one embodiment, a manipulation device is provided which includes an actuation mechanism having a floating and auto-locking pivot point. More specifically, FIGS. 5A-5D show an exemplary embodiment of a manipulation device 100 which includes an actuation mechanism 107 having first and second handles 108, 110 joined at a selectively movable pivot 114 that allows selective lateral positioning of the drive member 102 relative to the coupling member 106. As shown, the pivot point 114 is not a fixed pivot point but rather a freely floating pivot point 114 thereby allowing the drive member 102 to pivot relative to the coupling member 106 at any of a plurality of pivot points. Additionally, as will be shown, the device 100 can be configured to allow for an auto-locking pivot point 114. More specifically, the desired pivot point 114 can be automatically locked in response to application of an initial actuation force. For example, the pivot point 114 can lock in place as the second handle element 110 is squeezed in a direction towards the first handle element 108 thereby allowing the user to easily utilize the device 100.

The free-floating and/or auto-locking pivot point 114 can be provided in various manners. In one such embodiment, referring to FIGS. 5B-5D, one of the handle elements 108, 110 of the actuation mechanism 107, for example, the second handle element 110, can include a pin 118 extending out therefrom. Additionally, the first handle element 108 can include an elongate slot 116 formed therein. As will be described below, the pin 118 (in communication with at least one locking component 120) and/or the elongate slot 116 can be sized and configured so as to releasably engage one another. For example, the pin 118 can be in communication with a set of locking components 120 or the pin 118 can have such a locking component 120 integrally formed thereon thereby allowing the pin to lock relative to the elongate slot. Additionally, a support rod 112 can extend between the first and second handle elements 108, 110 wherein the support rod 112 can provide added stability and support to the actuation mechanism 107 independent of the position of the pivot point 114. As will be understood by those skilled in the art, the support rod 112 can be in communication with a compression and/or extension spring so as to allow the pin 118 and/or locking components 120 to remain "unlocked" relative to the elongate slot in the absence of an actuation force.

As shown, the pin 118 and the elongate slot 116 can be sized and configured such that the pin 118 can freely-slide along a desired length of the elongate slot 116. Further, the pin 118 and/or the slot 116 can be configured to lock relative to one another at any of a plurality of positions along a length of the slot 116 thereby defining a plurality of potential pivot points. Those skilled in the art will appreciate that the pin 118 and/or the elongate slot 116 can be configured in various manners so as to provide this auto-locking functionality. For example, in the illustrated exemplary embodiment, the pin 118 can include or be coupled to at least one locking component 120 having a plurality of seating areas, such as teeth, grooves, detents, and the like. Additionally, a corresponding set of seating areas 117 (shown in FIG. 5D) can be formed in and extend along a length of the elongate slot 116. Further, the pin 118, the elongate slot 116, and the corresponding sets of seating areas 117, 120 can be sized and configured such that application of an initial actuation force to the actuation mechanism (i.e., the second handle element 110 being squeezed towards the second handle element 108) can securely lock the position of the pin 118 relative to the elongate slot 116 thereby defining a pivot point 114. Upon removal of the manipulation force, the pin 118 can once again be capable of freely moving along the length of the elongate slot 116 until the pin 118 is positioned at the next desired pivot point whereupon the initial actuation force can be reapplied to the actuation mechanism thereby once again locking the pin 118 relative to the elongate slot 116 and thereby defining a second pivot point.

Figure 6A:
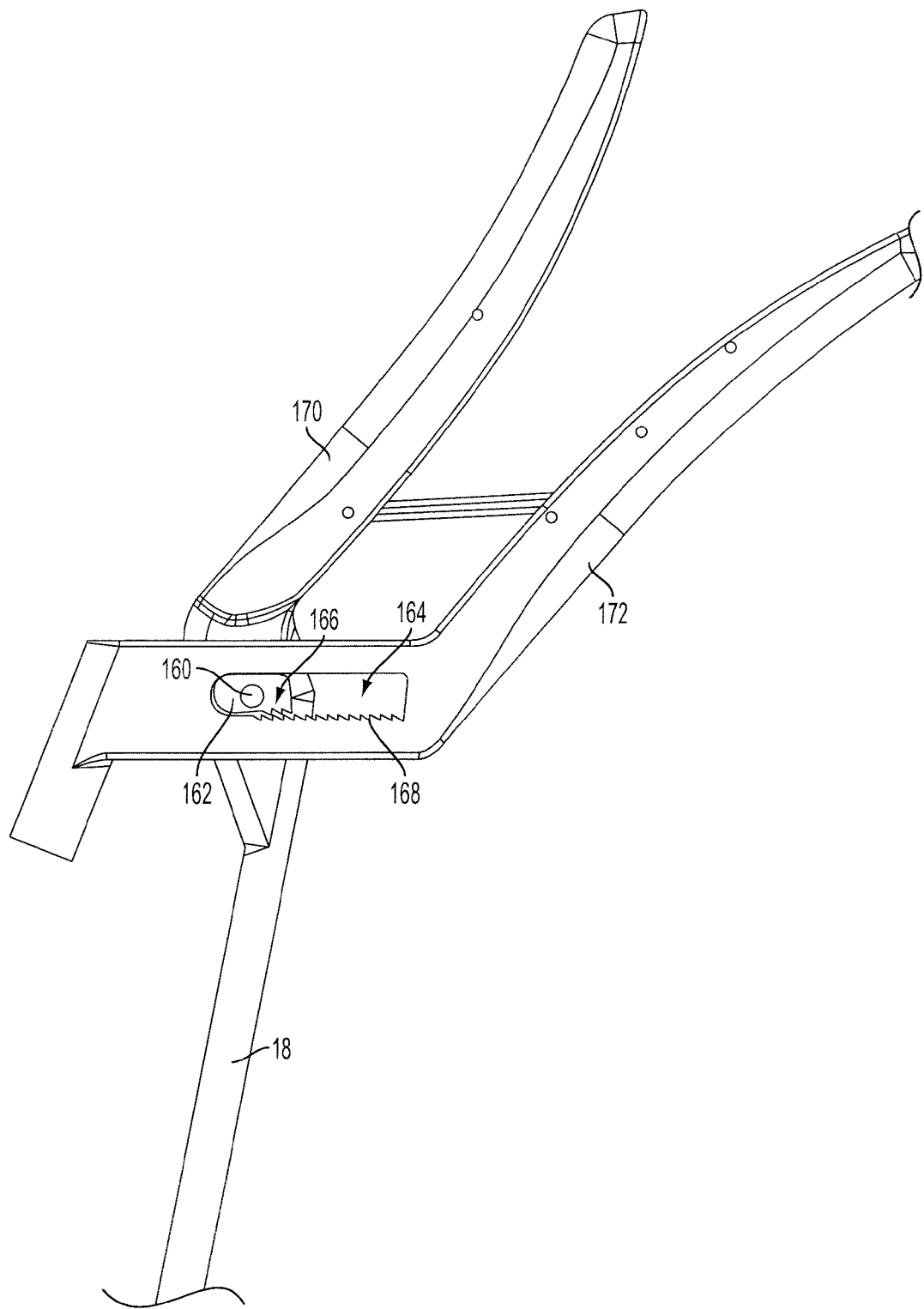
FIG. 6A is a perspective view of another embodiment of a manipulation device.
Figure 6B:
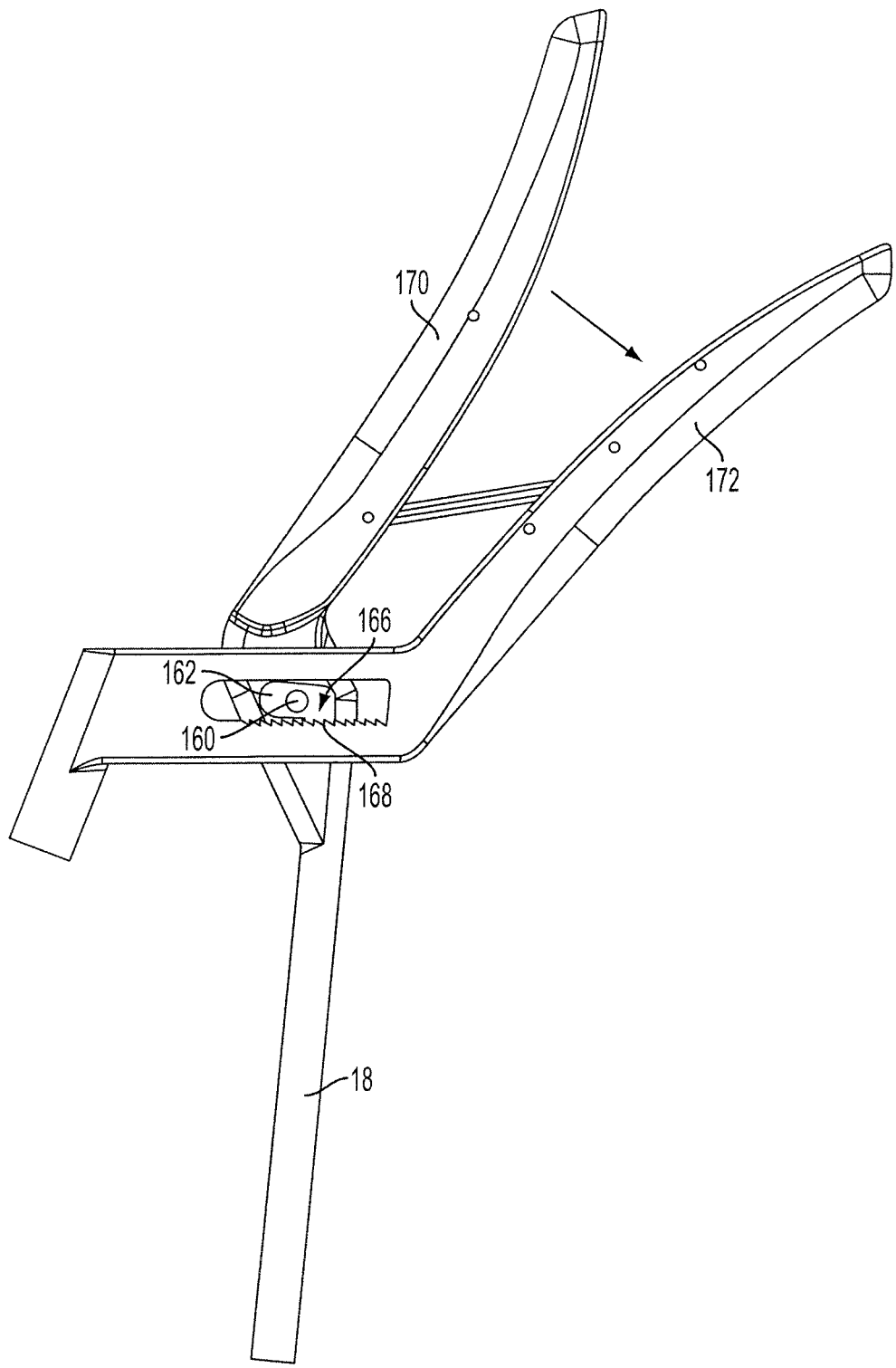
FIG. 6B is another perspective view of the embodiment of FIG. 6A.

FIGS. 6A-6B show another embodiment of an auto-locking pivot point. As shown in FIG. 6A, similar to above, one handle 170 can include a pin 160 configured to be received by an elongate slot 164 formed in another handle 172. Additionally, the pin 160 can be in communication with an engagement lever 162. As shown, the engagement lever 162 can include at least one seating area 166 formed on a portion thereof wherein this seating area 166 is capable of engaging a corresponding seating area 168 formed along a length of the elongate slot 164. As shown in FIG. 6A, the engagement lever 162 can be coupled to the pin 160 such that in the absence of an actuation force, the seating area 166 of the engagement lever 162 is biased away from the corresponding seating area 168 of the elongate slot 164. However, during application of the actuation force (shown in FIG. 6B as one handle 170 moving towards second handle 172), the seating area 166 of the engagement lever 162 can be configured to move towards (and ultimately into contact with) the corresponding seating area 168 of the elongate slot 164 thereby defining a pivot point for the drive member relative to the coupling member. Those skilled in the art will appreciate that various mechanisms are well known in the art for biasing the engagement lever in the manner described above (e.g., springs).

Figure 7A:
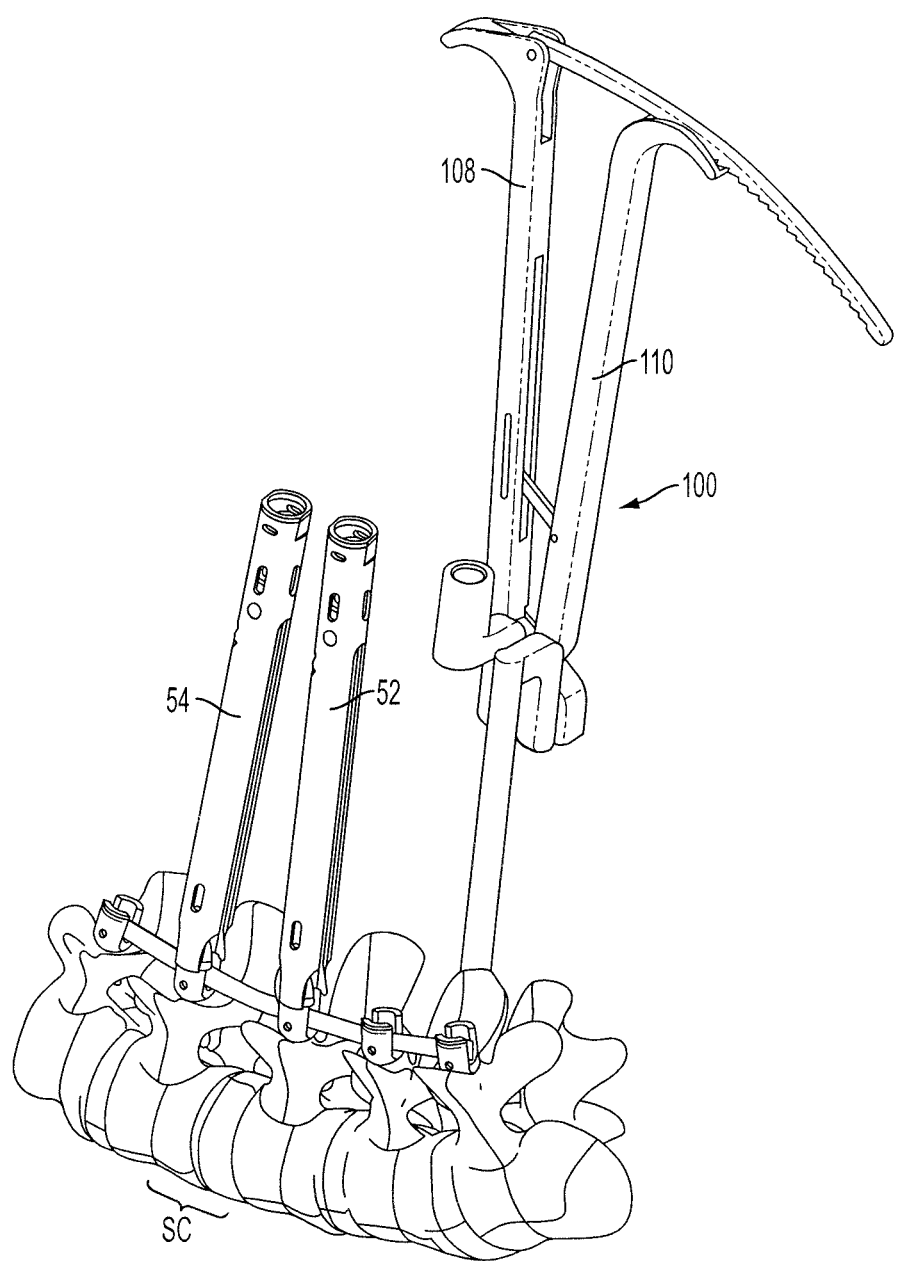
FIG. 7A is a representation of the manipulation device of FIG. 5A being delivered to a pair of surgical sleeves extending from a spinal construct.
Figure 7B:
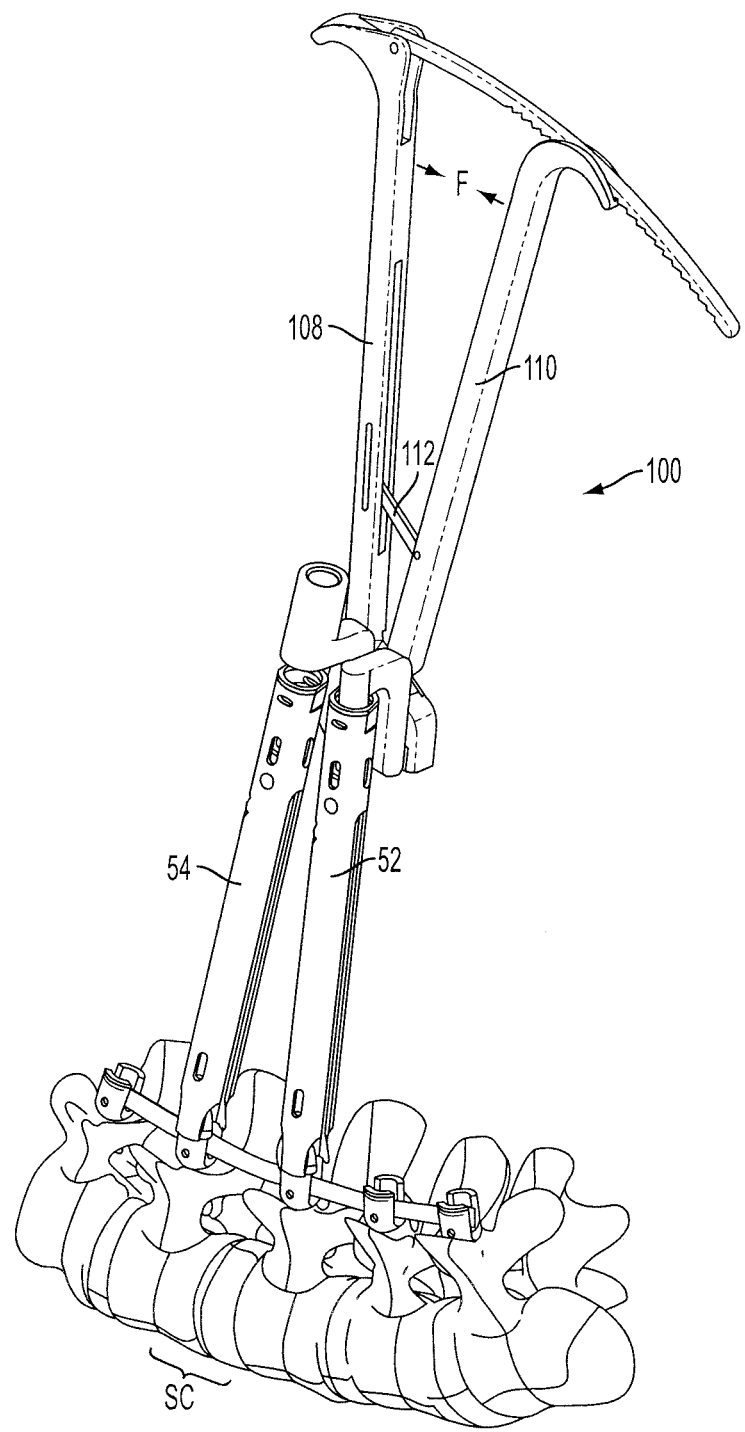
FIG. 7B is a representation of the manipulation device of FIG. 5A coupled to the surgical sleeves.
Figure 7C:
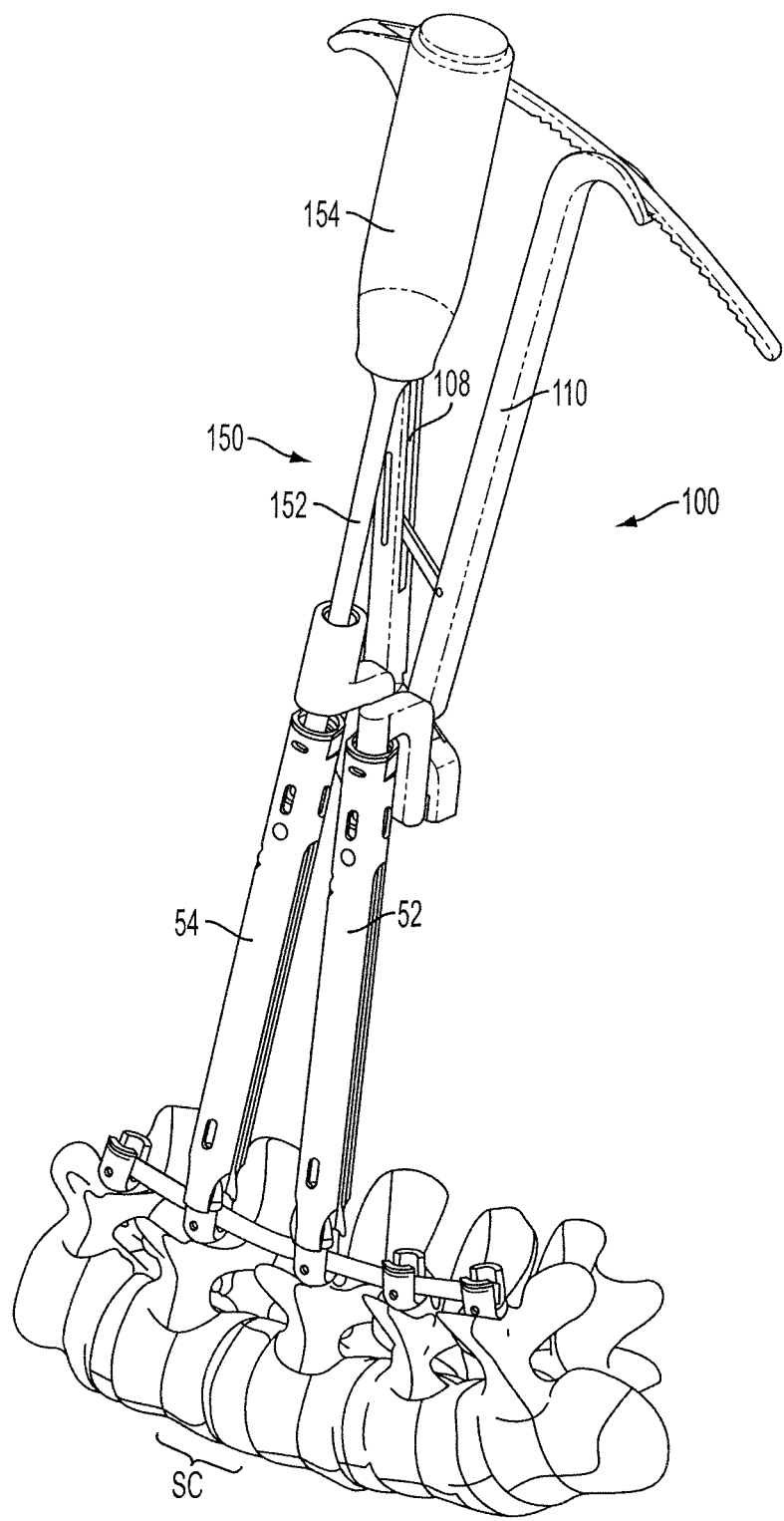
FIG. 7C is a representation of a driver in communication with the coupling member and being disposed within an inner lumen of the second surgical sleeve.
Figure 7D:
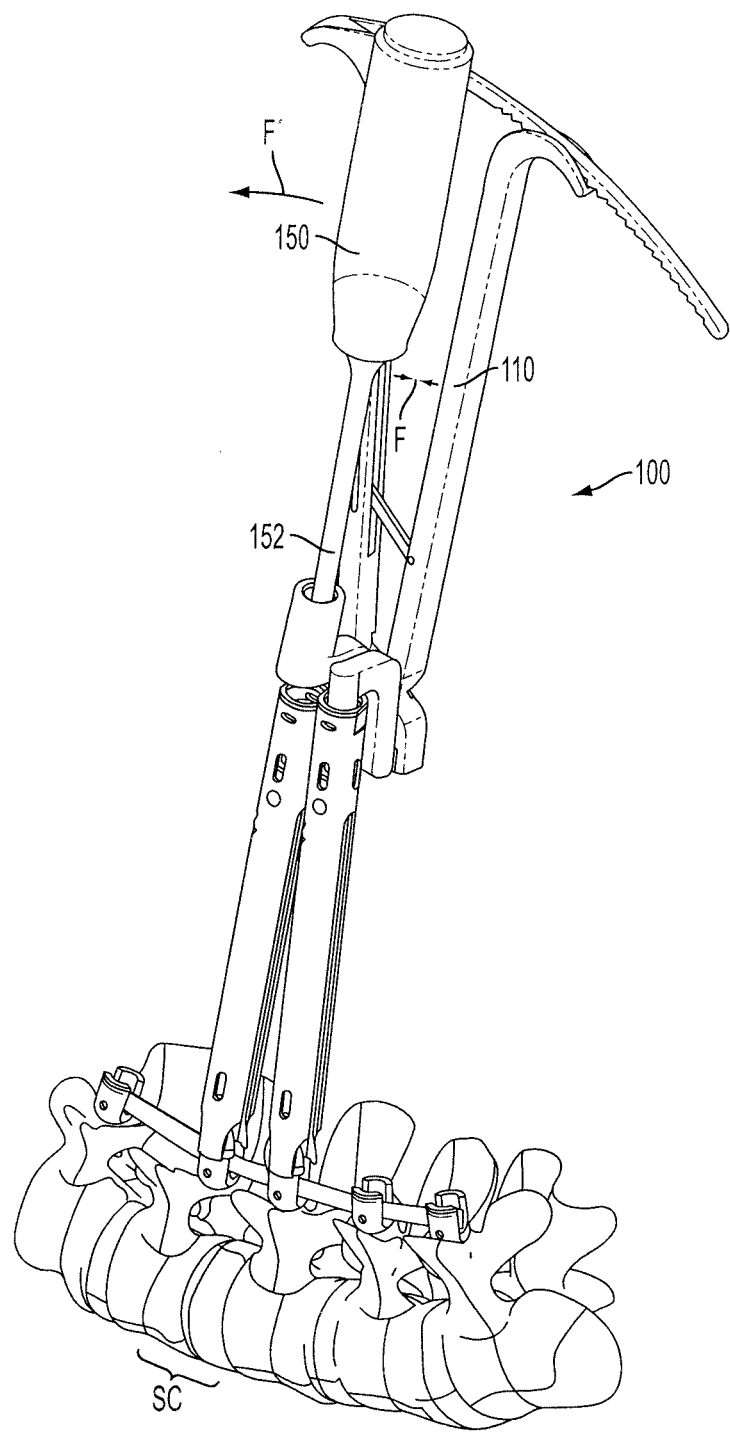
FIG. 7D is a representation of the driver and the manipulation device following compression of the spinal construct.

As described above, the system can also include a driver capable of delivering a set screw (not shown) to a bone anchor in communication with the unlocked sleeve, and can also be utilized, if desired, to provide an additional force to the spinal construct. As will be appreciated by those skilled in the art, the driver can be any device capable of being disposed within an inner lumen of the unlocked surgical sleeve and further be capable, if desired, of delivering the desired manipulation force to the spinal construct. For example, FIGS. 7C-7D show an exemplary embodiment of such a driver 150 being disposed through an opening of a coupling element 106 and further being positioned within an inner lumen of the unlocked sleeve 54. As shown, the driver 150 can include an elongate shaft 152 having a handle 154 formed at a proximal end thereof. The elongate shaft 152 of the driver 150 is typically of a length which allows a distal portion of the driver 150 to reside adjacent the spinal construct (SC) while also allowing the handle 154 to be user-accessible. In an exemplary embodiment, as shown, the handle 154 can be sized and shaped to be easily grasped by a user. For example, FIGS. 7C-7D provides an example of a compression procedure. As shown, the user can supply an actuation force F (see arrows in FIG. 7D) to the actuation mechanism by squeezing the second handle element 110 towards the first handle element 108 thereby pivoting the drive member 102 towards the coupling member 106. Additionally, if desired, the user can supply a second force F' (see arrow in FIG. 7D) to the handle 154 of the driver 150 thereby utilizing the pivot point of the actuation mechanism as a fulcrum. Thus, these two forces F, F' can work together to supply the desired manipulation force (in this example, a compression force) to the spinal construct SC.

Once the construct has been manipulated as desired, the driver can be configured to deliver a set screw (not shown) to the rod-receiving element of the second bone screw coupled to the unlocked sleeve 54 thereby locking the fixation rod thereto. The system can then be utilized to manipulate an additional spinal construct, if desired.

Additionally, a method for manipulating (compressing or distracting) a spinal construct is also provided. Typically, as shown in FIG. 4A, the first surgical sleeve 52 is "a locked sleeve" in that a set screw (not shown) has already been locked within an associated bone anchor 49 in order to secure a fixation element 53 thereto. In contrast, the second sleeve 54 is "an unlocked sleeve" in that a set screw (not shown) has yet to be locked to an associated bone anchor 51. Thus, during application of manipulation force, the unlocked sleeve 54 will move relative to the locked sleeve 52. Following the desired manipulation, the set screw of the unlocked sleeve 54 can be locked to the associated bone anchor 51 thereby securing the corrected position of the spinal construct SC.

Similar to above, the presently disclosed method allows a user to efficiently and reliably position a manipulation device relative to adjacent surgical sleeves extending from a spinal construct. For example, in one embodiment the method can utilize a modular manipulation device thereby facilitating positioning of the device relative to the adjacent surgical sleeves. More specifically, as shown in FIGS. 4A-4C, the method can include positioning a drive member 12 relative to a first surgical sleeve 52, and also positioning a coupling member 14 relative to a second surgical sleeve 54. Once these members 12, 14 are positioned as desired, at least one of the members 12, 14 (or both) can be releasably engaged to an actuation mechanism 16 effective to pivot the drive member 12 relative to the coupling member 14.

FIGS. 7C and 7D provides an example of a user supplying a compression force to a spinal construct. More specifically, once the manipulation device is positioned as desired, a driver 150 can be disposed within the inner lumen of the second sleeve 54 such that a handle 154 of the driver 150 is accessible to a user and therefore, if desired, capable of allowing a user to supply a force thereto. With the driver 150 and the manipulation device positioned as such, referring to FIG. 7D, a user can supply an actuation force F to the actuation mechanism by squeezing the second handle element 110 towards the first handle element 108. Typically, this actuation force F is sufficient to provide the desired manipulation of the spinal construct. If desired, a user can also supply a second force F' to the handle 154 of the driver 150 thereby forcing the driver 150 towards (see arrow) the first handle element 108. As the user supplies these forces F, F', the driver 150 will utilize the pivot point of the actuation mechanism as a fulcrum so as to drive the distal portion of the second sleeve 54 towards the distal portion of the first sleeve 52 thereby resulting in compression of the spinal construct SC. Typically, the distal portion of the drive member and the distal portion of the driver will be positioned as close as possible to the spinal contract thereby optimizing the manipulation force.

Similarly, the method can provide for distraction of the spinal construct SC. More specifically, the actuation mechanism can be configured in a nonscissors-like configuration such that the drive member and the coupling member can move away from one another as the actuation force is supplied to the actuation mechanism. Thus, as in the compression procedure described above, the user once again supplies a first force to the actuation mechanism by squeezing the second handle element 110 towards the first handle element 108. However, in the case of distraction, this actuation force will now result in the drive member pivoting away from the coupling member. Additionally, in contrast to above, if the user supplies an additional force via the driver, the user now forces the driver towards the second handle element 110 (i.e., the opposite direction as compared to compression). Like above, the driver can once again utilize the pivot point of the actuation mechanism as a fulcrum so as to force the distal portion of the second sleeve 54 away from the distal portion of the first sleeve 52 thereby resulting in distraction of the spinal construct SC.

Other embodiments of the method are also provided for enhancing a user's ability to couple the manipulation device to the surgical sleeves. For example, the method can include utilizing a manipulation device having an actuation mechanism, as shown in FIGS. 5A-5D, which includes first and second handles 108, 110 joined at a selectively movable pivot 114 that allows selective lateral positioning of the drive member 102 relative to the coupling member 106. Thus, the method can include positioning the drive member 102 relative to the first sleeve 52, laterally moving the coupling member 106 relative to the drive member 102 until the coupling member 106 is positioned as desired in relation to the second surgical sleeve 54, and locking the coupling member 106 relative to the drive member 102 so as to allow the members 102, 106 to pivot relative to one another at a desired pivot point. As described above and shown in FIG. 5D, the device can include an auto-locking functionality such that the desired pivot point can be selected by application of an initial actuation force and the member can be allowed to freely move as the initial actuation force is removed. Thus, in use, a surgeon can effectively select the desired pivot point and relative positioning of the drive member 102 and the coupling member 106 with a single hand (i.e., by squeezing or releasing the handles 108, 110 of the actuation mechanism). Following the positioning of the members 102, 106 and the selection of the pivot point, the method allows for manipulation of the spinal construct in the same manner as described above.

Any or all of the above-described steps can be performed as a minimally invasive surgical ("MIS") procedure or as an open procedure. In a MIS procedure, the desired manipulation of the spinal construct can be performed with minimal tissue and/or muscle trauma. For example, referring to FIG. 4A, in a MIS procedure, the first and second surgical sleeves 52, 54 can be percutaneous access devices which are delivered to adjacent vertebrae via first and second point incisions (not shown) with the proximal portion of each percutaneous access device 52, 54 being accessible to the surgeon. Thus, in use, the manipulation device and/or the driver can be coupled to the access devices without any additional muscle and/or tissue trauma thereby reducing patient recovery time as well as reducing any associated scarring.

One skilled in the art will appreciate further features and advantages of the presently disclosed system and method based on the above-described embodiments. Accordingly, the disclosed embodiments are not to be limited by what has been particularly shown and described, except as indicated by the appended claims. All publications and references cited herein are expressly incorporated herein by reference in their entirety.

What is claimed is:

1. A spinal manipulation device, comprising:
   a drive member having an elongate shaft which is sized and configured to be disposed within an inner lumen of a first surgical sleeve extending from a first vertebra;
   a coupling member being sized and configured to maintain a spatial relationship relative to a second surgical sleeve extending from a second vertebra as the coupling member moves relative to the drive member; and
   an actuation mechanism effective to pivot the drive member relative to the coupling member, the actuation mechanism including first and second handles joined at a selectively movable pivot that allows selective lateral positioning of the drive member relative to the coupling member, wherein the actuation mechanism is configured such that the lateral position of the movable pivot is locked automatically when the first and second handles are pivoted towards each other.

2. The device of claim 1, wherein the movable pivot includes an elongate slot formed on the first handle that is sized and configured to receive a pin extending from the second handle element, the pin being configured to releasably engage the elongate slot.

3. The device of claim 2, wherein the elongate slot includes a plurality of seating areas, each being sized and configured to seat and retain the pin at a desired position to create a desired pivot point.

4. The device of claim 1, further comprising a locking mechanism configured to lock the drive member relative to the coupling member.

5. The device of claim 4, wherein the locking mechanism includes a locking lever element extending from a proximal end of the second handle and configured to releasably engage a proximal end of the first handle.

6. The device of claim 1, wherein at least one of the drive member and the coupling member is releasably engaged to the actuation mechanism.

7. The device of claim 1, wherein the coupling member includes a retractable element configured to move from a retracted position to an extending position, the retractable element being positioned above the second surgical sleeve when in the refracted position, and extending along a length of the second surgical sleeve when in the extended position.

8. The device of claim 1, wherein the selectively moveable pivot comprises a pin in communication with a slot formed in one of the first and second handles, the pin being releasably engaged with the slot.

9. The device of claim 8, wherein the slot comprises a plurality of seating areas sized to receive the pin to lock the movable pivot.

10. The device of claim 8, wherein the pin comprises a locking component having a plurality of seating areas.

11. A spinal manipulation device, comprising:
a drive member having an elongate shaft which is sized and configured to be disposed within an inner lumen of a first surgical sleeve extending from a first vertebra;
a coupling member having a retractable element configured to move between a retracted position and an extended position, the coupling member configured to reside above a second surgical sleeve extending from a second vertebra thereby allowing the retractable element to enter an inner lumen of the second surgical sleeve as the retractable member moves from the retracted position to the extended position; and
an actuation mechanism effective to pivot the drive member relative to the coupling member,
wherein actuation of the actuation mechanism is effective to lock a lateral position of a selectively movable pivot coupling the drive member and the coupling member.

12. The device of claim 11, wherein the actuation mechanism includes first and second handles joined at the selectively movable pivot that allows selective lateral positioning of the drive member relative to the coupling member.

13. The device of claim 11, wherein the retractable element is a rod.

14. The device of claim 11,
wherein the movable pivot comprises an elongate slot and a pin, the pin being in communication with an engagement lever having at least one seating area configured to engage a corresponding seating area formed in the elongate slot.

15. A spinal manipulation device, comprising:
a drive member having an elongate shaft which is sized and configured to be disposed within an inner lumen of a first surgical sleeve extending from a first vertebra;
a coupling member having a retractable element configured to move between a retracted position and an extended position, the coupling member configured to reside above a second surgical sleeve extending from a second vertebra thereby allowing the retractable element to enter an inner lumen of the second surgical sleeve as the retractable member moves from the retracted position to the extended position; and
an actuation mechanism effective to pivot the drive member relative to the coupling member,
wherein the actuation mechanism includes first and second handles joined at a selectively movable pivot that allows selective lateral positioning of the drive member relative to the coupling member, and
wherein the movable pivot includes an elongate slot formed on the first handle that is sized and configured to receive a pin extending from the second handle element, the pin being in communication with an engagement lever having at least one seating area configured to engage to a corresponding seating area formed along a portion of the elongate slot.

16. The device of claim 15, wherein the seating area of the engagement lever is biased away from the corresponding seating area of the elongate slot in the absence of an actuation force.

17. The device of claim 16, wherein the seating area of the engagement lever is configured to move towards and into contact with the corresponding seating area of the elongate slot during application of the actuation force.

18. A method of manipulating a spinal construct, comprising:
disposing an elongate shaft of a drive member within an inner lumen of a first surgical sleeve extending from a first vertebra of a spinal construct;
positioning a coupling member adjacent a second surgical sleeve extending from a second vertebra of the spinal construct;
disposing a driver within an inner lumen of the second surgical sleeve; and
providing an actuation force to an actuation mechanism effective to pivot the drive member relative to the coupling member to provide a desired manipulation force to the spinal construct and to lock the lateral location of a selectively movable pivot that couples the drive member and the coupling member.

19. The method of claim 18, wherein the steps are performed in a minimally invasive surgical procedure.

20. The method of claim 18, wherein providing the actuation force to the actuation mechanism includes squeezing a second handle element of the actuation mechanism towards a first handle element of the actuation mechanism.

21. The method of claim 18, wherein the steps are performed in an open procedure.

* * * * *